(12) United States Patent
Boyd et al.

(10) Patent No.: US 7,687,524 B2
(45) Date of Patent: Mar. 30, 2010

(54) CATHEPSIN CYSTEINE PROTEASE INHIBITORS

(75) Inventors: Michael Boyd, Montreal (CA); Cheuk Lau, Ile Bizard (CA); Christophe Mellon, L'Ile Bizard (CA); Bruno Roy, Ile Bizard (CA); John Scheigetz, Dollard des Ormeaux (CA); Vouy Linh Truong, Pierrefonds (CA)

(73) Assignee: Merck Frosst Canada & Co., Quebec (CA)

( * ) Notice: Subject to any disclaimer, the term of this patent is extended or adjusted under 35 U.S.C. 154(b) by 428 days.

(21) Appl. No.: 10/581,692

(22) PCT Filed: Dec. 9, 2004

(86) PCT No.: PCT/CA2004/002101
§ 371 (c)(1),
(2), (4) Date: Jun. 6, 2006

(87) PCT Pub. No.: WO2005/056529
PCT Pub. Date: Jun. 23, 2005

(65) Prior Publication Data
US 2007/0099893 A1    May 3, 2007

Related U.S. Application Data

(60) Provisional application No. 60/529,254, filed on Dec. 12, 2003.

(51) Int. Cl.
*A61K 31/44* (2006.01)
*A61K 31/275* (2006.01)
*C07D 211/70* (2006.01)
*C07C 255/46* (2006.01)

(52) U.S. Cl. ............ 514/357; 514/521; 546/315; 558/410

(58) Field of Classification Search ............ 514/357, 514/521; 546/315; 558/410
See application file for complete search history.

(56) References Cited

U.S. PATENT DOCUMENTS

2008/0188529 A1* 8/2008 Bayly et al. ............ 514/357

FOREIGN PATENT DOCUMENTS

| CA | 2 306 313 | 5/1999 |
| CA | 2 439 415 | 9/2002 |
| CA | 2439415 A1 * | 9/2002 |
| CA | 2 477 657 | 9/2003 |
| CA | 2477657 A1 * | 9/2003 |
| WO | WO 03/075836 A2 * | 9/2003 |

OTHER PUBLICATIONS

Dufour, E et al., Biochemistry, vol. 34, pp. 9136-9143 (1995), "Peptide Aldehydes and Nitriles as Transition State Analog Inhibitors of Cysteine Proteases".

* cited by examiner

*Primary Examiner*—Joseph R Kosack
(74) *Attorney, Agent, or Firm*—Nicole M. Beeler; David A. Muthard

(57) ABSTRACT

This invention relates to a novel class of compounds which are cysteine protease inhibitors, including but not limited to, inhibitors of cathepsins K, L, S and B. These compounds are useful for treating diseases in which inhibition of bone resorption is indicated, such as osteoporosis.

9 Claims, No Drawings

CATHEPSIN CYSTEINE PROTEASE INHIBITORS

PRIORITY CLAIM

This application is a 371 National Stage Application of PCT/CA2004/002101, filed on Dec. 09, 2004, which claims priority from U.S. Provisional Application Ser. No. 60/529,254, filed on Dec. 12, 2003.

BACKGROUND OF THE INVENTION

A variety of disorders in humans and other mammals involve or are associated with abnormal bone resorption. Such disorders include, but are not limited to, osteoporosis, glucocorticoid induced osteoporosis, Paget's disease, abnormally increased bone turnover, periodontal disease, tooth loss, bone fractures, atherosclerosis, obesity, parasitic infection, rheumatoid arthritis, osteoarthritis, periprosthetic osteolysis, osteogenesis imperfecta, metastatic bone disease, hypercalcemia of malignancy, and multiple myeloma. One of the most common of these disorders is osteoporosis, which in its most frequent manifestation occurs in postmenopausal women. Osteoporosis is a systemic skeletal disease characterized by a low bone mass and microarchitectural deterioration of bone tissue, with a consequent increase in bone fragility and susceptibility to fracture. Osteoporotic fractures are a major cause of morbidity and mortality in the elderly population. Because osteoporosis, as well as other disorders associated with bone loss, are generally chronic conditions, it is believed that appropriate therapy will typically require chronic treatment.

Bone resorption is primarily performed by osteoclasts, which are multinuclear giant cells. Osteoclasts resorb bone by forming an initial cellular attachment to bone tissue, followed by the formation of an extracellular compartment or lacunae. The lacunae are maintained at a low pH by a proton-ATP pump. The acidified environment in the lacunae allows for initial demineralization of bone followed by the degradation of bone proteins or collagen by proteases such as cysteine proteases. See Delaisse, J. M. et al., 1980, *Biochem J* 192: 365-368; Delaisse, J. et al., 1984, *Biochem Biophys Res Commun*:441-447; Delaisse, J. M. et al., 1987, *Bone* 8:305-313, which are hereby incorporated by reference in their entirety. Collagen constitutes 95% of the organic matrix of bone. Therefore, proteases involved in collagen degradation are an essential component of bone turnover, and as a consequence, the development and progression of osteoporosis.

Cathepsins belong to the papain superfamily of cysteine proteases. These proteases function in the normal physiological as well as pathological degradation of connective tissue. Cathepsins play a major role in intracellular protein degradation and turnover and remodeling. To date, a number of cathepsin have been identified and sequenced from a number of sources. These cathepsins are naturally found in a wide variety of tissues. For example, cathepsin B, C, F, H, L, K, O, S, V, W, and Z have been cloned. Cathepsin K (which is also known by the abbreviation cat K) is also known as cathepsin O and cathepsin O2. See PCT Application WO 96/13523, Khepri Pharmaceuticals, Inc., published May 9, 1996, which is hereby incorporated by reference in its entirety. Cathepsin L is implicated in normal lysosomal proteolysis as well as several diseases states, including, but not limited to, metastasis of melanomas. Cathepsin S is implicated in Alzheimer's disease, asthma, atherosclerosis, chronic obstructive pulmonary disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogenic immune responses, including, but not limited to, rejection of organ transplants or tissue grafts. Increased Cathepsin B levels and redistribution of the enzyme are found in tumors, suggesting a role in tumor invasion and metastasis. In addition, aberrant Cathepsin B activity is implicated in such disease states as rheumatoid arthritis, osteoarthritis, pneumocystisis carinii, acute pancreatitis, inflammatory airway disease and bone and joint disorders.

Mammalian cathepsins are related to the papain-like cysteine proteases expressed by disease-causing parasites including those from the families protozoa, platyhelminthes, nematodes and arthropodes. These cysteine proteases play an essential role in the life cycle of these organisms.

Cysteine protease inhibitors such as E-64 (trans-epoxysuccinyl-L-leucylamide-(4-guanidino) butane) are known to be effective in inhibiting bone resorption. See Delaisse, J. M. et al., 1987, *Bone* 8:305-313, which is hereby incorporated by reference in its entirety. Recently, cathepsin K was cloned and found specifically expressed in osteoclasts See Tezuka, K. et al., 1994, *J Biol Chem* 269:1106-1109; Shi, G. P. et al., 1995, *FEBS Lett* 357:129-134; Bromme, D. and Okamoto, K., 1995, *Biol Chem Hoppe Seyler* 376:379-384; Bromme, D. et al., 1996, *J Biol Chem* 271:2126-2132; Drake, F. H. et al., 1996, *J Biol Chem* 271:12511-12516, which are hereby incorporated by reference in their entirety. Concurrent to the cloning, the autosomal recessive disorder, pycnodysostosis, characterized by an osteopetrotic phenotype with a decrease in bone resorption, was mapped to mutations present in the cathepsin K gene. To date, all mutations identified in the cathepsin K gene are known to eliminate collagenase activity. See Gelb, B. D. et al., 1996, *Science* 273:1236-1238; Johnson, M. R. et al., 1996, *Genome Res* 6:1050-1055; Hou, W.-S. et al., 1999 J. Clin. Invest. 103, 731-738 which are hereby incorporated by reference in their entirety. Therefore, it appears that cathepsin K is involved in osteoclast mediated bone resorption.

Human type I collagen, the major collagen in bone is a good substrate for cathepsin K. See Kafienah, W., et al., 1998, *Biochem J* 331:727-732, which is hereby incorporated by reference in its entirety. Accordingly, inhibitors of Cathepsin K can reduce bone resorption. Such inhibitors would be useful in treating disorders involving bone resorption, such as osteoporosis.

SUMMARY OF THE INVENTION

The present invention relates to compounds that are capable of treating or preventing cathepsin dependent conditions or disease states in a mammal in need thereof. One embodiment of the present invention is illustrated by a compound of Formula I, and the pharmaceutically acceptable salts, esters, stereoisomers and N-oxide derivatives thereof:

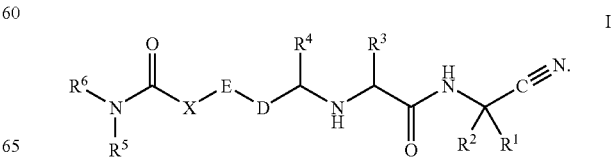

DETAILED DESCRIPTION OF THE INVENTION

The present invention relates to compounds of the following chemical formula:

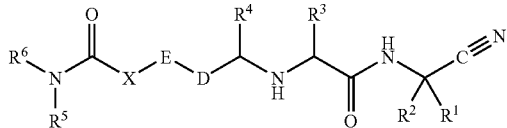

wherein $R^1$ is hydrogen, $C_{1-6}$ alkyl or $C_{2-6}$ alkenyl wherein said alkyl and alkenyl groups are optionally substituted with one to six halo, $C_{3-6}$ cycloalkyl, —$SR^7$, —$SOR^7$, —$SO_2R^7$, —$SO_2CH(R^a)(R^b)$, —$OR^7$, —$N(R^7)_2$, aryl, heteroaryl or heterocyclyl wherein said aryl, heteroaryl and heterocyclyl groups are optionally substituted with one or two substitutents independently selected from $C_{1-6}$ alkyl, halo, hydroxyalkyl, hydroxy, alkoxy or keto;

$R^2$ is hydrogen, $C_{1-6}$ alkyl or $C_{2-6}$ alkenyl wherein said alkyl and alkenyl groups are optionally substituted with one to six halo, $C_{3-6}$ cycloalkyl, —$SR^7$, —$SOR^7$, —$SO_2R^7$, —$SO_2CH(R^a)(R^b)$, —$OR^7$, —$N(R^7)_2$, aryl, heteroaryl or heterocyclyl wherein said aryl, heteroaryl and heterocyclyl groups are optionally substituted with one or two substitutents independently selected from $C_{1-6}$ alkyl, halo, hydroxyalkyl, hydroxy, alkoxy or keto;

or $R^1$ and $R^2$ can be taken together with the carbon atom to which they are attached to form a $C_{3-8}$ cycloalkyl or heterocyclyl ring wherein said ring system is optionally substituted with one or two substituents independently selected from $C_{1-6}$ alkyl, hydroxyalkyl, haloalkyl, or halo;

$R^3$ is $C_{1-6}$ alkyl or $C_{2-6}$ alkenyl, wherein said alkyl and alkenyl groups are optionally substituted with $C_{3-6}$ cycloalkyl or one to six halo;

$R^4$ is $C_{1-6}$ alkyl substituted with 1-6 halo;

$R^5$ is selected from hydrogen or $C_{1-3}$ alkyl;

D is aryl or heteroaryl, wherein said aryl or heteroaryl group, which may be monocyclic or bicyclic, is optionally substituted on either the carbon or the heteroatom with one to five substituents independently selected from $C_{1-6}$ alkyl, haloalkyl, halo, keto, alkoxy, —$SR^7$, —$OR^7$, $N(R^7)_2$, —$SO_2R^7$, or —$SO_2R^a$;

E is aryl or heteroaryl, wherein said aryl or heteroaryl group, which may be monocyclic or bicyclic, is optionally substituted on either the carbon or the heteroatom with one to five substituents independently selected from $C_{1-6}$ alkyl, haloalkyl, halo, keto, alkoxy, —$SR^7$, —$OR^7$, $N(R^7)_2$ or —$SO_2R^7$;

X is $CR^aR^b$ or $C_{3-8}$ cycloalkyl;

$R^7$ is selected from hydrogen, $C_{1-6}$ alkyl, aryl, aryl($C_{1-4}$)alkyl, heteroaryl, heteroaryl($C_{1-4}$)alkyl, $C_{3-8}$cycloalkyl, $C_{3-8}$cycloalkyl($C_{1-4}$)alkyl, and heterocyclyl($C_{1-4}$)alkyl wherein said groups can be optionally substituted with one, two, or three substituents independently selected from halo, alkoxy, cyano, —$NR^aR^b$, —$SR^a$ or —$SO_mR^a$;

$R^6$ is selected from hydrogen, $C_{1-6}$ alkyl, $C_{3-8}$ cycloalkyl, heterocyclyl, heteroaryl, cyano, halo, alkoxy, —$OR^a$, —$NR^a$, —$SR^a$ or —$SO_mR^5$; wherein said alkyl, cycloalkyl, heterocyclyl and heteroaryl groups can be optionally substituted with one, two, or three substituents independently selected from halo, cyano or —$OR^a$;

$R^a$ is hydrogen or $C_{1-6}$ alkyl which is optionally substituted with one, two, or three substituents independently selected from halo or —$OR^5$;

$R^b$ is hydrogen or $C_{1-6}$ alkyl which is optionally substituted with one, two, or three substituents independently selected from halo or —$OR^5$;

m is an integer from zero to two;

or a pharmaceutically acceptable salts, stereoisomers and N-oxide derivatives thereof.

In one class of the invention, $R^1$ and $R^2$ can be taken together with the carbon atom to which they are attached to form a $C_{3-8}$ cycloalkyl ring.

In another class of the invention, $R^3$ is $C_{1-6}$ alkyl which is optionally substituted with one to six halo.

In another class of the invention, D is aryl. In a subclass of the invention, D is phenyl.

In another class of the invention, X is $C_{3-8}$ cycloalkyl. In a subclass of the invention, X is cyclopropyl.

Reference to the preferred embodiments set forth above is meant to include all combinations of particular and preferred groups unless stated otherwise.

Specific embodiments of the present invention include, but are not limited to:

$N^1$-(1-cyanocyclopropyl)-$N^2$-[(1S)-1-(4'-{1-[(cyclopropylamino)carbonyl]cyclopropyl}-2'-fluorobiphenyl-4-yl)-2,2,2-trifluoroethyl]-4-fluoro-L-leucinamide;

$N^2$-((1S)-1-{4'-[1-(azetidin-1-ylcarbonyl)cyclopropyl]biphenyl-4-yl}-2,2-difluoroethyl)-$N^1$-(1-cyanocyclopropyl)-4-fluoro-L-leucinamide;

$N^1$-(1-cyanocyclopropyl)-$N^2$-{(1S)-2,2-difluoro-1-[4'-(1-{[(2,2,2-trifluoroethyl)amino]carbonyl}cyclopropyl)biphenyl-4-yl]ethyl}-4-fluoro-L-leucinamide;

$N^1$-(1-cyanocyclopropyl)-$N^2$-((1S)-1-{4'-[2-(cyclopropylamino)-2-oxoethyl]biphenyl-4-yl}-2,2-difluoroethyl)-4-fluoro-L-leucinamide;

$N^1$-(1-cyanocyclopropyl)-$N^2$-[(1S)-2,2-difluoro-1-(4'-{1-[(isopropylamino)carbonyl]cyclopropyl}biphenyl-4-yl)ethyl]-4-fluoro-L-leucinamide;

$N^1$-(1-cyanocyclopropyl)-$N^2$-[(1S)-2,2-difluoro-1-(4'-{1-[(pyridin-3-ylamino)carbonyl]cyclopropyl}biphenyl-4-yl)ethyl]-4-fluoro-L-leucinamide;

$N^1$-(1-cyanocyclopropyl)-$N^2$-{(1S)-2,2-difluoro-1-[4'-(1-{[(2-hydroxyethyl)amino]carbonyl}cyclopropyl)biphenyl-4-yl]ethyl}-4-fluoro-L-leucinamide;

$N^1$-(1-cyanocyclopropyl)-$N^2$-{(1S)-2,2-difluoro-1-[4'-(1-{[(1-methylcyclopropyl)amino]carbonyl}cyclopropyl)biphenyl-4-yl]ethyl}-4-fluoro-L-leucinamide;

$N^1$-(1-cyanocyclopropyl)-$N^2$-{(1S)-2,2-difluoro-1-[4'-(1-{[(2,2,2-trifluoro-1-methylethyl)amino]carbonyl}cyclopropyl)biphenyl-4-yl]ethyl}-4-fluoro-L-leucinamide;

$N^1$-(1-cyanocyclopropyl)-$N^2$-{(1S)-2,2-difluoro-1-[4'-(1-{[(2-fluorocyclopropyl)amino]carbonyl}cyclopropyl)biphenyl-4-yl]ethyl}-4-fluoro-L-leucinamide;

$N^1$-(1-cyanocyclopropyl)-$N^2$-[(1S)-2,2-difluoro-1-(4'-{1-[(1,3-thiazol-2-ylamino)carbonyl]cyclopropyl}biphenyl-4-yl)ethyl]-4-fluoro-L-leucinamide;

$N^2$-{(1S)-1-[4'-(2-amino-1,1-difluoro-2-oxoethyl)biphenyl-4-yl]-2,2,2-trifluoroethyl}-$N^1$-(1-cyanocyclopropyl)-4-fluoro-L-leucinamide;

$N^1$-(1-cyanocyclopropyl)-$N^2$-[(1S)-1-(4'-{1-[(cyclopropylamino)carbonyl]cyclopropyl}biphenyl-4-yl)-2,2,2-trifluoroethyl]-4-fluoro-L-leucinamide;

$N^1$-(cyanomethyl)-$N^2$-[(1S)-1-(4'-{1-[(cyclopropylamino)carbonyl]cyclopropyl}biphenyl-4-yl)-2,2,2-trifluoroethyl]-4-fluoro-L-leucinamide;

$N^2$-((1S)-1-{4'-[1-(aminocarbonyl)cyclopropyl]-2'-fluorobiphenyl-4-yl}-2,2,2-trifluoroethyl)-$N^1$-(1-cyanocyclopropyl)-

$N^1$-(1-cyanocyclopropyl)-$N^2$-[(1S)-1-(4'-{1-[(cyclopropylamino)carbonyl]cyclopropyl}biphenyl-4-yl)-2,2-difluoroethyl]-L-leucinamide;

$N^1$-(1-cyanocyclopropyl)-$N^2$-{(1S)-2,2-difluoro-1-[4'-(1-{[(2,2,2-trifluoroethyl)amino]carbonyl}cyclopropyl)biphenyl-4-yl]ethyl}-L-leucinamide;

$N^2$-((1S)-1-{4'-[1-(aminocarbonyl)cyclopropyl]biphenyl-4-yl}-2,2-difluoroethyl)-$N^1$-(1-cyanocyclopropyl)-L-leucinamide;

$N^1$-(1-cyanocyclopropyl)-$N^2$-[(1S)-1-(4'-{1-[(cyclopropylamino)carbonyl]cyclobutyl}biphenyl-4-yl)-2,2,2-trifluoroethyl]-4-fluoro-L-leucinamide;

$N^2$-((1S)-1-{4'-[1-(aminocarbonyl)cyclobutyl]biphenyl-4-yl}-2,2,2-trifluoroethyl)-$N^1$-(cyanomethyl)-4-fluoro-L-leucinamide;

$N^2$-((1S)-1-{4'-[1-(aminocarbonyl)cyclobutyl]biphenyl-4-yl}-2,2-difluoroethyl)-$N^1$-(1-cyanocyclopropyl)-4-fluoro-L-leucinamide;

$N^1$-(1-cyanocyclopropyl)-$N^2$-{(1S)-1-[4'-(1-{[(1-cyanocyclopropyl)amino]carbonyl}cyclopropyl)biphenyl-4-yl]-2,2-difluoroethyl}-L-leucinamide;

$N^1$-(1-cyanocyclopropyl)-$N^2$-[(1S)-2,2-difluoro-1-(4'-{1-[(methoxyamino)carbonyl]cyclopropyl}biphenyl-4-yl)ethyl]-L-leucinamide;

$N^1$-(1-cyanocyclopropyl)-$N^2$-{(1S)-2,2-difluoro-1-[4'-(1-{[methoxy(methyl)amino]carbonyl}cyclopropyl)biphenyl-4-yl]ethyl}-L-leucinamide;

$N^1$-(1-cyanocyclopropyl)-$N^2$-{(1S)-2,2-difluoro-1-[4'-(1-{[(2-hydroxyethyl)amino]carbonyl}cyclopropyl)biphenyl-4-yl]ethyl}-L-leucinamide;

$N^1$-(1-cyanocyclopropyl)-$N^2$-[(1S)-1-(4'-{1-[(dimethylamino)carbonyl]cyclopropyl}biphenyl-4-yl)-2,2-difluoroethyl]-4-fluoro-L-leucinamide;

$N^1$-(1-cyanocyclopropyl)-$N^2$-[(1S)-1-(4'-{1-[(cyclobutylamino)carbonyl]cyclopropyl}biphenyl-4-yl)-2,2-difluoroethyl]-4-fluoro-L-leucinamide;

$N^1$-(1-cyanocyclopropyl)-$N^2$-((1S)-2,2-difluoro-1-{4'-[1-(pyrrolidin-4-ylcarbonyl)cyclopropyl]biphenyl-4-yl}ethyl)-4-fluoro-L-leucinamide;

$N^1$-(1-cyanocyclopropyl)-$N^2$-{(1S)-2,2-difluoro-1-{4'-[1-(pyrrolidin-1-ylcarbonyl}cyclopropyl]biphenyl-4-yl}ethyl)-4-fluoro-L-leucinamide;

$N^1$-(1-cyanocyclopropyl)-$N^2$-{(1S)-2,2-difluoro-1-[4'-(1-{[methoxy(methyl)amino]carbonyl}cyclopropyl)biphenyl-4-yl]ethyl}-4-fluoro-L-leucinamide;

$N^1$-(1-cyanocyclopropyl)-$N^2$-{(1S)-2,2-difluoro-1-[4'-(1-{[(2-methoxyethyl)amino]carbonyl}cyclopropyl)biphenyl-4-yl]ethyl}-4-fluoro-L-leucinamide;

$N^1$-(1-cyanocyclopropyl)-$N^2$-((1S)-2,2-difluoro-1-{4'-[1-(morpholin-4-ylcarbonyl)cyclopropyl]biphenyl-4-yl}ethyl)-4-fluoro-L-leucinamide;

$N^1$-(1-cyanocyclopropyl)-$N^2$-[(1S)-2,2-difluoro-1-(4'-{1-[(methylamino)carbonyl]cyclopropyl}biphenyl-4-yl)ethyl]-4-fluoro-L-leucinamide;

$N^1$-(1-cyanocyclopropyl)-$N^2$-{(1S)-1-[4'-(1-{[(cyclopropylmethyl)amino]carbonyl}cyclopropyl)biphenyl-4-yl]-2,2-difluoroethyl}-4-fluoro-L-leucinamide;

$N^1$-(1-cyanocyclopropyl)-$N^2$-[(1S)-2,2-difluoro-1-(4'-{1-[(propylamino)carbonyl]cyclopropyl}biphenyl-4-yl)ethyl]-4-fluoro-L-leucinamide;

$N^2$-((1S)-1-{4'-[1-(aminocarbonyl)cyclopropyl]biphenyl-4-yl}-2,2,2-trifluoroethyl)-$N^1$-(1-cyanocyclopropyl)-4-fluoro-L-leucinamide;

$N^1$-(1-cyanocyclopropyl)-$N^2$-{(1S)-1-[4'-(1-{[(cyanomethyl)amino]carbonyl}cyclopropyl)biphenyl-4-yl]-2,2,2-trifluoroethyl}-4-fluoro-L-leucinamide;

$N^1$-(1-cyanocyclopropyl)-4-fluoro-$N^2$-{(1S)-2,2,2-trifluoro-1-[4'-(1-{[(methylsulfonyl)amino]carbonyl}cyclopropyl)biphenyl-4-yl]ethyl}-L-leucinamide;

$N^2$-[(1S)-1-(4'-{1-[(tert-butylamino)carbonyl]cyclopropyl}biphenyl-4-yl)-2,2,2-trifluoroethyl]-$N^1$-(1-cyanocyclopropyl)-4-fluoro-L-leucinamide;

$N^1$-(1-cyanocyclopropyl)-$N^2$-((1S)-1-{4'-[2-(cyclopropylamino)-1,1-dimethyl-2-oxoethyl]biphenyl-4-yl}-2,2,2-trifluoroethyl)-4-fluoro-L-leucinamide;

$N^1$-(1-cyanocyclopropyl)-$N^2$-[(1S)-1-(4'-{1-[(cyclopropylamino)carbonyl]cyclopropyl}-3'-fluorobiphenyl-4-yl)-2,2,2-trifluoroethyl]-4-fluoro-L-leucinamde;

$N^1$-(1-cyanocyclopropyl)-$N^2$-[(1S)-1-(4'-{1-[(cyclopropylamino)carbonyl]cyclopropyl}biphenyl-4-yl)-2,2,2-trifluoroethyl]-L-leucinamide;

$N^1$-(1-cyanocyclopropyl)-$N^2$-[(1S)-1-(4'-{1-[(cyclopropylamino)carbonyl]cyclopropyl}-3'-fluorobiphenyl-4-yl)-2,2-difluoroethyl]-4-fluoro-L-leucinamide;

$N^1$-(1-cyanocyclopropyl)-$N^2$-((1S)-1-{4'-[2-(cyclopropylamino)-1,1-dimethyl-2-oxoethyl]biphenyl-4-yl}-2,2-difluoroethyl)-4-fluoro-L-leucinamide;

$N^1$-(1-cyanocyclopropyl)-$N^2$-[(1S)-1-(4'-{1-[(cyclopropylamino)carbonyl]cyclopropyl}-2'-fluorobiphenyl-4-yl)-2,2-difluoroethyl]-4-fluoro-L-leucinamide;

$N^1$-(1-cyanocyclopropyl)-4-fluoro-$N^2$-{(1S)-2,2,2-trifluoro-1-[4'-(1-{[(2-fluorocyclopropyl)amino]carbonyl}cyclopropyl)biphenyl-4-yl]ethyl}-L-leucinamide;

$N^2$-[(1S)-1-(4-{5-[1-(aminocarbonyl)cyclopropyl]-3-chloropyridin-2-yl}phenyl)-2,2,2-trifluoroethyl]-$N^1$-(1-cyanocyclopropyl)-4-fluoro-L-leucinamide;

$N^2$-{(1S)-1-[4-(3-chloro-5-{1-[(cyclopropylamino)carbonyl]cyclopropyl}pyridin-2-yl)phenyl]-2,2,2-trifluoroethyl}-$N^1$-(1-cyanocyclopropyl)-4-fluoro-L-leucinamide;

$N^1$-(1-cyanocyclopropyl)-$N^2$-{(1S)-1-[4-(5-{1-[(cyclopropylamino)carbonyl]cyclopropyl}pyridin-2-yl)phenyl]-2,2,2-trifluoroethyl}-4-fluoro-L-leucinamide;

$N^2$-((1S)-1-{4'-[1-(aminocarbonyl)cyclopropyl]biphenyl-4-yl}-2,2,2-trifluoroethyl)-$N^1$-(cyanomethyl)-4-fluoro-L-leucinamide;

$N^2$-[(1S)-1-(4-{5-[1-(aminocarbonyl)cyclopropyl]pyridin-2-yl}phenyl)-2,2,2-trifluoroethyl]-$N^1$-(cyanomethyl)-4-fluoro-L-leucinamide;

$N^2$-{(1S)-1-[4'-(2-amino-1-methyl-2-oxoethyl)biphenyl-4-yl]-2,2,2-trifluoroethyl}-$N^1$-(1-cyanocyclopropyl)-4-fluoro-L-leucinamide;

$N^2$-((1S)-1-{4'-[(1R)-2-amino-1-methyl-2-oxoethyl]biphenyl-4-yl}-2,2,2-trifluoroethyl)-$N^1$-(1-cyanocyclopropyl)-4-fluoro-L-leucinamide;

$N^2$-((1S)-1-{4'-[(1S)-2-amino-1-methyl-2-oxoethyl]biphenyl-4-yl}-2,2,2-trifluoroethyl)-$N^1$-(1-cyanocyclopropyl)-4-fluoro-L-leucinamide;

$N^2$-{(1S)-1-[4'-(2-amino-1-methyl-2-oxoethyl)-2'-fluorobiphenyl-4-yl]-2,2,2-trifluoroethyl}-$N^1$-(1-cyanocyclopropyl)-4-fluoro-L-leucinamide;

$N^2$-((1S)-1-{4-[5-(2-amino-1-methyl-2-oxoethyl)pyridin-2-yl]phenyl}-2,2,2-trifluoroethyl)-$N^1$-(1-cyanocyclopropyl)-4-fluoro-L-leucinamide;

$N^2$-{(1S)-1-[4'-(2-amino-1-methyl-2-oxoethyl)-2'-fluorobiphenyl-4-yl]-2,2-difluoroethyl}-$N^1$-(1-cyanocyclopropyl)-4-fluoro-L-leucinamide;

$N^2$-((1S)-1-{4'-[(1R)-2-amino-1-methyl-2-oxoethyl]-2'-fluorobiphenyl-4-yl}-2,2,2-trifluoroethyl)-$N^1$-(1-cyanocyclopropyl)-4-fluoro-L-leucinamide;

$N^2$-((1S)-1-{4'-[(1S)-2-amino-1-methyl-2-oxoethyl]-2'-fluorobiphenyl-4-yl}-2,2,2-trifluoroethyl)-$N^1$-(1-cyanocyclopropyl)-4-fluoro-L-leucinamide;

N²-((1S)-1-{4'-[(1S)-2-amino-1-methyl-2-oxoethyl]-2-bromobiphenyl-4-yl}-2,2,2-trifluoroethyl)-N¹-(1-cyanocyclopropyl)-4-fluoro-L-leucinamide;

N²-((1S)-1-{4'-[(1S)-2-amino-1-methyl-2-oxoethyl]biphenyl-4-yl}-2,2,2-trifluoroethyl)-N¹-(1-cyanocyclopropyl)-4-fluoro-5-hydroxy-L-leucinamide;

1-(4'-{(1S)-1-[((1S)-1-{[(1-cyanocyclopropyl)amino]carbonyl}-3,3,3-trifluoropropyl)amino]-2,2,2-trifluoroethyl}biphenyl-4-yl)cyclopropanecarboxamide;

N²-((1S)-1-{4'-[1-(aminocarbonyl)vinyl]biphenyl-4-yl}-2,2,2-trifluoroethyl)-N¹-(1-cyanocyclopropyl)-4-fluoro-L-leucinamide;

N²-((1S)-1-{4'-[1-(aminocarbonyl)cyclopropyl]biphenyl-4-yl}-2,2,2-trifluoroethyl)-N¹-(1-cyanocyclopropyl)-L-norvalinamide;

N²-((1S)-1-{4'-[1-(2-amino-2-oxoethyl)cyclopropyl]biphenyl-4-yl}-2,2,2-trifluoroethyl)-N¹-(1-cyanocyclopropyl)-4-fluoro-L-leucinamide;

N²-{(1S)-1-[4'-(3-amino-2,2-dimethyl-3-oxopropyl)biphenyl-4-yl]-2,2,2-trifluoroethyl}-N¹-(1-cyanocyclopropyl)-4-fluoro-L-leucinamide;

N²-{(1S)-1-[4'-(2-amino-2-oxoethyl)-2'-fluorobiphenyl-4-yl]-2,2,2-trifluoroethyl}-N¹-(1-cyanocyclopropyl)-4-fluoro-L-leucinamide;

N²-{(1S)-1-[4'-(2-amino-2-oxoethyl)biphenyl-4-yl]-2,2,2-trifluoroethyl}-N¹-(1-cyanocyclopropyl)-4-fluoro-L-leucinamide;

or a pharmaceutically acceptable salts, esters, stereoisomers or N-oxide derivatives thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application, alone or in combination with any other disclosed compound. These and other aspects of the invention will be apparent from the teachings contained herein.

Utilities

The compounds of the present invention are inhibitors of cathepsins and are therefore useful to treat or prevent cathepsin dependent diseases or conditions in mammals, preferably humans. Specifically, the compounds of the present invention are selective inhibitors of Cathepsin K in that they are at least 100 fold selective over cathepsins B, L, S and F, and are useful to treat or prevent Cathepsin K dependent diseases or conditions in mammals, preferably humans.

"Cathepsin dependent diseases or conditions" refers to pathologic conditions that depend on the activity of one or more cathepsins. "Cathepsin K dependent diseases or conditions" refers to pathologic conditions that depend on the activity of Cathepsin K. Diseases associated with Cathepsin K activities include osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, atherosclerosis and cancer including metastatic bone disease, hypercalcemia of malignancy, and multiple myeloma. In treating such conditions with the instantly claimed compounds, the required therapeutic amount will vary according to the specific disease and is readily ascertainable by those skilled in the art. Although both treatment and prevention are contemplated by the scope of the invention, the treatment of these conditions is the preferred use.

An embodiment of the invention is a method of inhibiting cathepsin activity in a mammal in need thereof, comprising administering to the mammal a therapeutically effective amount of any of the compounds or any of the pharmaceutical compositions described above.

A class of the embodiment is the method wherein the cathepsin activity is cathepsin K activity.

Another embodiment of the invention is a method of treating or preventing cathepsin dependent conditions in a mammal in need thereof, comprising administering to the mammal a therapeutically effective amount of any of the compounds or any of the pharmaceutical compositions described above.

A class of the embodiment is the method wherein the cathepsin activity is cathepsin K activity.

Another embodiment of the invention is a method of inhibiting bone loss in a mammal in need thereof, comprising administering to the mammal a therapeutically effective amount of any of the compounds or any of the pharmaceutical compositions described above. Another embodiment of the invention is a method of reducing bone loss in a mammal in need thereof, comprising administering to the mammal a therapeutically effective amount of any of the compounds or any of the pharmaceutical compositions described above. The utility of cathepsin K inhibitors in the inhibition of bone resorption is known in the literature, see Stroup, G. B., Lark, M. W., Veber, D F., Bhattacharrya, A., Blake, S., Dare, L. C., Erhard, K. F., Hoffman, S. J., James, I. E., Marquis, R. w., Ru, Y., Vasko-Moser, J. A., Smith, B. R., Tomaszek, T. and Gowen, M. Potent and selective inhibition of human cathepsin K leads to inhibition of bone resorption in vivo in a nonhuman primate. J. Bone Miner. Res., 16:1739-1746;2001; and Votta, B. J., Levy, M. A., Badger, A., Dodds, R. A., James, I. E., Thompson, S., Bossard, M. J., Carr, T., Connor, J. R., Tomaszek, T. A., Szewczuk, L., Drake, F. H., Veber, D., and Gowen, M. Peptide aldehyde inhibitors of cathepsin K inhibit bone resorption both in vivo and in vitro. J. Bone Miner. Res. 12:1396-1406; 1997.

Another embodiment of the invention is a method of treating or preventing osteoporosis in a mammal in need thereof, comprising administering to the mammal a therapeutically effective amount of any of the compounds or any of the above pharmaceutical compositions described above. The utility of cathepsin K inhibitors in the treatment or prevention of osteoporosis is known in the literature, see Saftig, P., Hunziker, E., Wehmeyer, O., Jones, S., Boyde, A., Rommerskirch, W., Moritz, J. D., Schu, P., and Vonfigura, K. Impaired osteoclast bone resorption leads to osteopetrosis in cathepsin K-deficient mice. Proc. Natl. Acad. Sci. USA 95:13453-13458; 1998.

Another embodiment of the invention is a method of treating or preventing rheumatoid arthritic condition in a mammal in need thereof, comprising administering to the mammal a therapeutically effective amount of any of the compounds or any of the pharmaceutical compositions described above. It is known in the literature that progressive destruction of the periarticular bone is a major cause of joint dysfunction and disability in patients with rheumatoid arthritis (RA), see Goldring SR, "Pathogenesis of bone erosions in rheumatoid arthritis". Curr. Opin. Rheumatol. 2002; 14: 406-10. Analysis of joint tissues from patients with RA have provided evidence that cathepsin K positive osteoclasts are the cell types that mediate the focal bone resorption associated with rheumatoid synovial lesion, see Hou, W-S, Li, W, Keyszer, G, Weber, E, Levy, R, Klein, M J, Gravallese, E M, Goldring, S R, Bromme, D, "Comparision of Cathepsin K and S expression within the Rheumatoid and Osteoarthritic Synovium", Arthritis Rheumatism 2002; 46: 663-74. In addition, generalized bone loss is a major cause of morbidity associated with severe RA. The frequency of hip and spinal fractures is substantially increased in patients with chronic RA, see Gould A, Sambrook, P, Devlin J et al, "Osteoclastic activation is the principal mechanism leading to secondary osteoporosis in rheumatoid arthritis". J. Rheumatol. 1998; 25: 1282-9. The utility of cathepsin K inhibitors in the treatment or prevention of resorption in subarticular bone and of generalized bone loss represent a rational approach for pharmacological intervention on the progression of rheumatoid arthritis.

Another embodiment of the invention is a method of treating or preventing the progression of osteoarthritis in a mammal in need thereof, comprising administering to the mammal a therapeutically effective amount of any of the compounds or any of the pharmaceutical compositions described above. It is known in the literature that osteoarthritis (OA) is accompanied with a well-defined changes in the joints, including erosion of the articular cartilage surface, peri-articular endochondral ossification/osteophytosis, and subchondral bony sclerosis and cyst formation, see Oettmeier R, Abendroth, K, "Osteoarthritis and bone: osteologic types of osteoarthritis of the hip", Skeletal Radiol. 1989; 18: 165-74. Recently, the potential contribution of subchondral bone sclerosis to the initiation and progression of OA have been suggested. Stiffened subchondral bone as the joint responding to repetitive impulsive loading, is less able to attenuate and distribute forces through the joint, subjecting it to greater mechanical stress across the articular cartilage surface. This in turn accelerates cartilage wear and fibrillate, see Radin, E L and Rose R M, "Role of subchondral bone in the initiation and progression of cartilage damage", Clin. Orthop. 1986; 213: 34-40. Inhibition of excessive subarticular bone resorption by an anti-resorptive agent such as a cathepsin K inhibitor, will lead to inhibition of subchondral bone turnover, thus may have a favorable impact on OA progression. In addition to the above hypothesis, cathepsin K protein expression was recently identified in synovial fibroblasts, macrophage-like cells, and chondrocytes from synovium and articular cartilage specimens derived from OA patients, see Hou, W-S, Li, W, Keyszer, G, Weber, E, Levy, R, Klein, M J, Gravallese, E M, Goldring, S R, Bromme, D, "Comparison of Cathepsin K and S expression within the Rheumatoid and Osteoarthritic Synovium", Arthritis Rheumatism 2002; 46: 663-74; and Dodd, R A, Connor, J R, Drake, F H, Gowen, M, "Expression of Cathepsin K messenger RNA in giant cells and their precursors in human osteoarthritic synovial tissues". Arthritis Rheumatism 1999; 42: 1588-93; and Konttinen, Y T, Mandelin, J, Li, T-F, Salo, J, Lassus, J et al. "Acidic cysteine endoproteinase cathepsin K in the degeneration of the superficial articular hyaline cartilage in osteoarthritis", Arthritis Rheumatism 2002; 46: 953-60. These recent studies thus implicated the role of cathepsin K in the destruction of collagen type II in the articular cartilage associated with the progression of osteoarthritis. The utility of cathepsin K inhibitors in the treatment or prevention of osteoarthritis as described in this invention thus comprise of two different mechanisms, one is on the inhibition of osteoclast-driven subchondral bone turnover, and two is on the direct inhibition of collagen type II degeneration in the synovium and cartilage of patients with OA.

Another embodiment of the invention is a method of treating cancer in a mammal in need thereof, comprising administering to the mammal a therapeutically effective amount of any of the compounds or any of the pharmaceutical compositions described above. It is known in the literature that cathepsin K is expressed in human breast carcinoma, prostate cancer and chordoma and has matrix degrading capabilities, see Littlewood-Evans A J, Bilbe G, Bowler W B, Farley D, Wlodarski B, Kokubo T, Inaoka T, Sloane J, Evans D B, Gallagher J A, "The osteoclast-associated protease cathepsin K is expressed in human breast carcinoma." Cancer Res 1997 Dec. 1;57(23):5386-90, Brubaker K D, Vessella R L, True L D, Thomas R., Corey E. "Cathepsin K mRNA and protein expression in prostate cancer progression." J Bone Miner Res 2003 18, 222-30, Haeckel C, Krueger S, Kuester D, Ostertag H, Samii M, Buehling F, Broemme D, Czerniak B, Roessner A. "Expression of cathepsin K in chordoma." Hum Pathol 2000 July;31(7):834-40.

Another embodiment of the invention is a method treating atherosclerosis in a mammal in need thereof, comprising administering to the mammal a therapeutically effective amount of any of the compounds or any of the pharmaceutical compositions described above. It is known in the literature that cathepsin K is expressed in human atheroma and has significant elastase activity, see Sukhova G K, Shi G P, Simon D I, Chapman H A, Libby P. "Expression of the elastolytic cathepsins S and K in human atheroma and regulation of their production in smooth muscle cells." J Clin Invest 1998 August 102, 576-83.

Another embodiment of the invention is a method treating obesity in a mammal in need thereof, comprising administering to the mammal a therapeutically effective amount of any of the compounds or any of the pharmaceutical compositions described above. It is known in the literature that cathepsin K mRNA is increased in adipose tissue in several mouse models of obesity and also in adipose tissue of obese human males, see Chiellini C, Costa M, Novelli S E, Amri E Z, Benzi L, Bertacca A, Cohen P, Del Prato S, Friedman J M, Maffei M. "Identification of cathepsin K as a novel marker of adiposity in white adipose tissue." J Cell Physiol 2003, 195, 309-21.

Another embodiment of the invention is a method of treating parasitic infections in a mammal in need thereof, comprising administering to the mammal a therapeutically effective amount of any of the compounds or any of the pharmaceutical compositions described above. It is known in the literature that mammalian cathepsins are related to the papain-like cysteine proteases which play an important role in the life cycle of these parasites. Such parasites are involved in the diseases of malaria, American trypanosomiasis, African trypanosomiasis, leishmaniasis, giardiasis, trichomoniasis, amoebiasis, schistosomiasis, fascioliasis, paragonimiasis and intestinal roundworms, see Lecaille F, Kaleta J, Bromme D., Human and parasitic papain-like cysteine proteases: their role in physiology and pathology and recent developments in inhibitor design. Chem Rev 2002 102, 4459-88.

Another embodiment of the invention is a method of treating mammalian diseases associated with cathepsin S including Alzheimer's disease, atherosclerosis, chronic obstructive pulmonary disease, cancer and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogenic immune responses, including, but not limited to, rejection of organ transplants or tissue grafts. It is known in the literature that cathepsin S activity is associated with the above disease states, see Munger J S, Haass C, Lemere C A, Shi G P, Wong W S, Teplow D B, Selkoe D J, Chapman H A. Lysosomal processing of amyloid precursor protein to A beta peptides: a distinct role for cathepsin S. Biochem J 1995 311, 299-305, Sukhova G K, Zhang Y, Pan J H, Wada Y, Yamamoto T, Naito M, Kodama T, Tsimikas S, Witztum J L, Lu M L, Sakara Y, Chin M T, Libby P, Shi G P. Deficiency of cathepsin S reduces atherosclerosis in LDL receptor-deficient mice. J Clin Invest 2003 111, 897-906, Zheng T, Zhu Z, Wang Z, Homer R J, Ma B, Riese R J Jr, Chapman H A Jr, Shapiro S D, Elias J A. Inducible targeting of IL-13 to the adult lung causes matrix metalloproteinase- and cathepsin-dependent emphysema. J Clin Invest 2000 106, 1081-93, Shi G P, Sukhova G K, Kuzuya M, Ye Q, Du J, Zhang Y, Pan J H, Lu M L, Cheng X W, Iguchi A, Perrey S, Lee A M, Chapman H A, Libby P. Deficiency of the cysteine protease cathepsin S impairs microvessel growth. Circ Res 2003 92, 493-500, Nakagawa T Y, Brissette W H, Lira P D, Griffiths R J, Petrushova N, Stock J, McNeish J D, Eastman S E, Howard E D, Clarke S R, Rosloniec E F, Elliott E A, Rudensky A Y. Impaired invariant chain degradation and antigen presentation and diminished collagen-induced arthritis in cathepsin S null mice. Immunity 1999 10, 207-17.

Exemplifying the invention is the use of any of the compounds described above in the preparation of a medicament for the treatment or prevention of osteoporosis in a mammal in need thereof. Still further exemplifying the invention is the use of any of the compounds described above in the preparation of a medicament for the treatment or prevention of: bone loss, bone resorption, bone fractures, metastatic bone disease or disorders related to cathepsin functioning.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

In the case of tablets for oral use, carriers which are commonly used include lactose and corn starch, and lubricating agents, such as magnesium stearate, are commonly added. For oral administration in capsule form, useful diluents include lactose and dried corn starch. For oral use of a therapeutic compound according to this invention, the selected compound may be administered, for example, in the form of tablets or capsules, or as an aqueous solution or suspension. For oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. When aqueous suspensions are required for oral use, the active ingredient is combined with emulsifying and suspending agents. If desired, certain sweetening or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The instant compounds are also useful in combination with known agents useful for treating or preventing osteoporosis, glucocorticoid induced osteoporosis, Paget's disease, abnormally increased bone turnover, periodontal disease, tooth loss, bone fractures, atherosclerosis, obesity, parasitic infection, rheumatoid arthritis, osteoarthritis, periprosthetic osteolysis, osteogenesis imperfecta, metastatic bone disease, hypercalcemia of malignancy, and multiple myeloma. Combinations of the presently disclosed compounds with other agents useful in treating or preventing osteoporosis or other bone disorders are within the scope of the invention. A person of ordinary skill in the art would be able to discern which combinations of agents would be useful based on the particular characteristics of the drugs and the disease involved. Such agents include the following: an organic bisphosphonate; an estrogen receptor modulator; an androgen receptor modulator; an inhibitor of osteoclast proton ATPase; an inhibitor of HMG-CoA reductase; an integrin receptor antagonist; an osteoblast anabolic agent, such as PTH; and the pharmaceutically acceptable salts and mixtures thereof. A preferred combination is a compound of the present invention and an organic bisphosphonate. Another preferred combination is a compound of the present invention and an estrogen receptor modulator. Another preferred combination is a compound of the present invention and an androgen receptor modulator. Another preferred combination is a compound of the present invention and an osteoblast anabolic agent.

"Organic bisphosphonate" includes, but is not limited to, compounds of the chemical formula

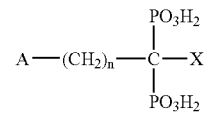

wherein n is an integer from 0 to 7 and wherein A and X are independently selected from the group consisting of H, OH, halogen, $NH_2$, SH, phenyl, C1-C30 alkyl, C3-C30 branched or cycloalkyl, bicyclic ring structure containing two or three N, C1-C30 substituted alkyl, C1-C10 alkyl substituted $NH_2$, C3-C10 branched or cycloalkyl substituted $NH_2$, C1-C10 dialkyl substituted $NH_2$, C1-C10 alkoxy, C1-C10 alkyl substituted thio, thiophenyl, halophenylthio, C1-C10 alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a C3-C10 ring.

In the foregoing chemical formula, the alkyl groups can be straight, branched, or cyclic, provided sufficient atoms are selected for the chemical formula. The C1-C30 substituted alkyl can include a wide variety of substituents, nonlimiting examples which include those selected from the group consisting of phenyl, pyridyl, furanyl, pyrrolidinyl, imidazonyl, $NH_2$, C1-C10 alkyl or dialkyl substituted $NH_2$, OH, SH, and C1-C10 alkoxy.

The foregoing chemical formula is also intended to encompass complex carbocyclic, aromatic and hetero atom structures for the A or X substituents, nonlimiting examples of which include naphthyl, quinolyl, isoquinolyl, adamantyl, and chlorophenylthio.

Pharmaceutically acceptable salts and derivatives of the bisphosphonates are also useful herein. Non-limiting examples of salts include those selected from the group consisting alkali metal, alkaline metal, ammonium, and mono-, di-, tri-, or tetra-C1-C30-alkyl-substituted ammonium. Preferred salts are those selected from the group consisting of sodium, potassium, calcium, magnesium, and ammonium salts. More preferred are sodium salts. Non-limiting examples of derivatives include those selected from the group consisting of esters, hydrates, and amides.

It should be noted that the terms "bisphosphonate" and "bisphosphonates", as used herein in referring to the therapeutic agents of the present invention are meant to also encompass diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated. Because of the mixed nomenclature currently in use by those of ordinary skill in the art, reference to a specific weight or percentage of a bisphosphonate compound in the present invention is on an acid active weight basis, unless indicated otherwise herein. For example, the phrase "about 5 mg of a bone resorption inhibiting bisphosphonate selected from the group consisting of alendronate, pharmaceutically acceptable salts thereof, and mixtures thereof, on an alendronic acid active weight basis" means that the amount of the bisphosphonate compound selected is calculated based on 5 mg of alendronic acid.

Non-limiting examples of bisphosphonates useful herein include the following:

Alendronic acid, 4-amino-1-hydroxybutylidene-1,1-bisphosphonic acid.

Alendronate (also known as alendronate sodium or alendronate monosodium trihydrate), 4-amino-1-hydroxybutylidene-1,1-bisphosphonic acid monosodium trihydrate.

Alendronic acid and alendronate are described in U.S. Pat. No. 4,922,007, to Kieczykowski et al., issued May 1, 1990; U.S. Pat. No. 5,019,651, to Kieczykowski et al., issued May 28, 1991; U.S. Pat. No. 5,510,517, to Dauer et al., issued Apr. 23, 1996; U.S. Pat. No. 5,648,491, to Dauer et al., issued Jul. 15, 1997, all of which are incorporated by reference herein in their entirety.

Cycloheptylaminomethylene-1,1-bisphosphonic acid, YM 175, Yamanouchi (incadronate, formerly known as cimadronate), as described in U.S. Pat. No. 4,970,335, to Isomura et al., issued Nov. 13, 1990, which is incorporated by reference herein in its entirety.

1,1-dichloromethylene-1,1-diphosphonic acid (clodronic acid), and the disodium salt (clodronate, Procter and Gamble), are described in Belgium Patent 672,205 (1966) and *J. Org. Chem* 32, 4111 (1967), both of which are incorporated by reference herein in their entirety.

1-hydroxy-3-(1-pyrrolidinyl)-propylidene-1,1-bisphosphonic acid (EB-1053).

1-hydroxyethane-1,1-diphosphonic acid (etidronic acid).

1-hydroxy-3-(N-methyl-N-pentylamino)propylidene-1,1-bisphosphonic acid, also known as BM-210955, Boehringer-Mannheim (ibandronate), is described in U.S. Pat. No. 4,927,814, issued May 22, 1990, which is incorporated by reference herein in its entirety.

1-hydroxy-2-imidazo-(1,2-a)pyridin-3-yethylidene (minodronate).

6-amino-1-hydroxyhexylidene-1,1-bisphosphonic acid (neridronate).

3-(dimethylamino)-1-hydroxypropylidene-1,1-bisphosphonic acid (olpadronate).

3-amino-1-hydroxypropylidene-1,1-bisphosphonic acid (pamidronate).

[2-(2-pyridinyl)ethylidene]-1,1-bisphosphonic acid (piridronate) is described in U.S. Pat. No. 4,761,406, which is incorporated by reference in its entirety.

1-hydroxy-2-(3-pyridinyl)-ethylidene-1,1-bisphosphonic acid (risedronate).

(4-chlorophenyl)thiomethane-1,1-disphosphonic acid (tiludronate) as described in U.S. Pat. No. 4,876,248, to Breliere et al., Oct. 24, 1989, which is incorporated by reference herein in its entirety.

1-hydroxy-2-(1H-imidazol-1-yl)ethylidene-1,1-bisphosphonic acid (zoledronate).

Nonlimiting examples of bisphosphonates include alendronate, cimadronate, clodronate, etidronate, ibandronate, incadronate, minodronate, neridronate, olpadronate, pamidronate, piridronate, risedronate, tiludronate, and zolendronate, and pharmaceutically acceptable salts and esters thereof. A particularly preferred bisphosphonate is alendronate, especially a sodium, potassium, calcium, magnesium or ammonium salt of alendronic acid. Exemplifying the preferred bisphosphonate is a sodium salt of alendronic acid, especially a hydrated sodium salt of alendronic acid. The salt can be hydrated with a whole number of moles of water or non whole numbers of moles of water. Further exemplifying the preferred bisphosphonate is a hydrated sodium salt of alendronic acid, especially when the hydrated salt is alendronate monosodium trihydrate.

It is recognized that mixtures of two or more of the bisphosphonate actives can be utilized.

The precise dosage of the organic bisphosphonate will vary with the dosing schedule, the particular bisphosphonate chosen, the age, size, sex and condition of the mammal or human, the nature and severity of the disorder to be treated, and other relevant medical and physical factors. Thus, a precise pharmaceutically effective amount cannot be specified in advance and can be readily determined by the caregiver or clinician. Appropriate amounts can be determined by routine experimentation from animal models and human clinical studies. Generally, an appropriate amount of bisphosphonate is chosen to obtain a bone resorption inhibiting effect, i.e. a bone resorption inhibiting amount of the bisphosphonate is administered. For humans, an effective oral dose of bisphosphonate is typically from about 1.5 to about 6000 μg/kg body weight and preferably about 10 to about 2000 μg/kg of body weight.

For alendronate monosodium trihydrate, common human doses which are administered are generally in the range of about 2 mg/day to about 40 mg/day, preferably about 5 mg/day to about 40 mg/day. In the U.S. presently approved dosages for alendronate monosodium trihydrate are 5 mg/day for preventing osteoporosis, 10 mg/day for treating osteoporosis, and 40 mg/day for treating Paget's disease.

In alternative dosing regimens, the bisphosphonate can be administered at intervals other than daily, for example once-weekly dosing, twice-weekly dosing, biweekly dosing, and twice-monthly dosing. In a once weekly dosing regimen, alendronate monosodium trihydrate would be administered at dosages of 35 mg/week or 70 mg/week.

"Selective estrogen receptor modulators" refers to compounds which interfere or inhibit the binding of estrogen to the receptor, regardless of mechanism. Examples of estrogen receptor modulators include, but are not limited to, estrogen, progestogen, estradiol, droloxifene, raloxifene, lasofoxifene, TSE-424, tamoxifen, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

An "estrogen receptor beta modulator" is a compound that selectively agonizes or antagonizes estrogen receptor beta (ERβ). Agonizing ERβ increases transcription of the tryptophan hydroxylase gene (TPH, the key enzyme in serotonin synthesis) via an ERβ mediated event. Examples of estrogen receptor beta agonists can be found in PCT International publication WO 01/82923, which published on Nov. 08, 2001, and WO 02/41835, which published on May 20, 2002, both of which are hereby incorporated by reference in their entirety.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"An inhibitor of osteoclast proton ATPase" refers to an inhibitor of the proton ATPase, which is found on the apical membrane of the osteoclast, and has been reported to play a significant role in the bone resorption process. This proton pump represents an attractive target for the design of inhibitors of bone resorption which are potentially useful for the treatment and prevention of osteoporosis and related metabolic diseases. See C. Farina et al., "Selective inhibitors of the osteoclast vacuolar proton ATPase as novel bone antiresorptive agents," DDT, 4: 163-172 (1999)), which is hereby incorporated by reference in its entirety.

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30-33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180, 589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885, 314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

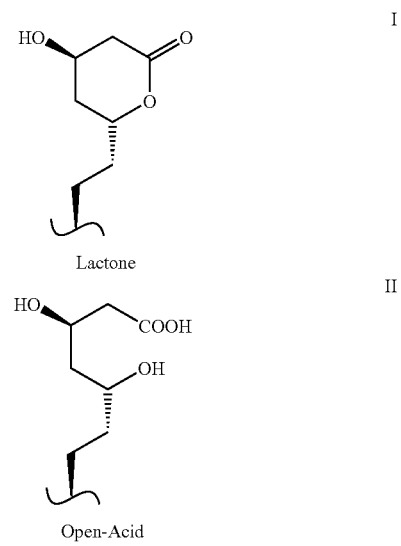

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenz-imidazole, diethylamine, piperazine, and tris(hydroxymethyl)aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

As used above, "integrin receptor antagonists" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. H. N. Lode and coworkers in PNAS USA 96: 1591-1596 (1999) have observed synergistic effects between an antiangiogenic αv integrin antagonist and a tumor-specific antibody-cytokine (interleukin-2) fusion protein in the eradication of spontaneous tumor metastases. Their results suggested this combination as having potential for the treatment of cancer and metastatic tumor growth. $\alpha_v\beta_3$ integrin receptor antagonists inhibit bone resorption through a new mechanism distinct from that of all currently available drugs. Integrins are heterodimeric transmembrane adhesion receptors that mediate cell-cell and cell-matrix interactions. The α and β integrin subunits interact non-covalently and bind extracellular matrix ligands in a divalent cation-dependent manner. The most abundant integrin on osteoclasts is $\alpha_v\beta_3$ ($>10^7$/osteoclast), which appears to play a rate-limiting role in cytoskeletal organization important for cell migration and polarization. The $\alpha_v\beta_3$ antagonizing effect is selected from inhibition of bone resorption, inhibition of restenosis, inhibition of macular degeneration, inhibition of arthritis, and inhibition of cancer and metastatic growth.

"An osteoblast anabolic agent" refers to agents that build bone, such as PTH. The intermittent administration of parathyroid hormone (PTH) or its amino-terminal fragments and analogues have been shown to prevent, arrest, partially reverse bone loss and stimulate bone formation in animals and humans. For a discussion refer to D. W. Dempster et al., "Anabolic actions of parathyroid hormone on bone," Endocr Rev 14: 690-709 (1993). Studies have demonstrated the clinical benefits of parathyroid hormone in stimulating bone formation and thereby increasing bone mass and strength. Results were reported by R M Neer et al., in New Eng J Med 344 1434-1441 (2001).

In addition, parathyroid hormone-related protein fragments or analogues, such as PTHrP-(1-36) have demonstrated potent anticalciuric effects [see M. A. Syed et al., "Parathyroid hormone-related protein-(1-36) stimulates renal tubular calcium reabsorption in normal human volunteers: implications for the pathogenesis of humoral hypercalcemia of malignancy," JCEM 86: 1525-1531 (2001)] and may also have potential as anabolic agents for treating osteoporosis.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents. The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The terms "treating" or "treatment" of a disease as used herein includes: preventing the disease, i.e. causing the clinical symptoms of the disease not to develop in a mammal that may be exposed to or predisposed to the disease but does not yet experience or display symptoms of the disease; inhibiting the disease, i.e., arresting or reducing the development of the disease or its clinical symptoms; or relieving the disease, i.e., causing regression of the disease or its clinical symptoms.

The term "bone resorption," as used herein, refers to the process by which osteoclasts degrade bone.

The present invention also encompasses a pharmaceutical composition useful in the treatment of osteoporosis or other bone disorders, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for a cathepsin dependent condition. Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittant throughout the dosage regimen.

The compounds of the present invention can be used in combination with other agents useful for treating cathepsin-mediated conditions. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating cathepsin-mediated conditions includes in principle any combination with any pharmaceutical composition useful for treating disorders related to estrogen functioning.

The scope of the invention therefore encompasses the use of the instantly claimed compounds in combination with a second agent selected from: an organic bisphosphonate; an estrogen receptor modulator; an androgen receptor modulator; an inhibitor of osteoclast proton ATPase; an inhibitor of HMG-CoA reductase; an integrin receptor antagonist; an osteoblast anabolic agent, such as PTH; and the pharmaceutically acceptable salts and mixtures thereof.

These and other aspects of the invention will be apparent from the teachings contained herein.

Definitions

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

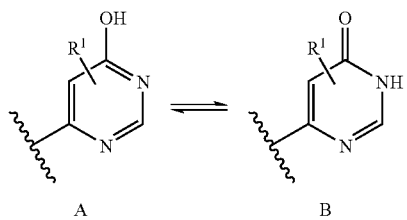

A       B

When any variable (e.g. R1, $R^2$, Ra etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring carbon atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

As used herein, "alkyl" is intended to include both branched and straight-chain saturated aliphatic hydrocarbon groups having one to ten carbon atoms unless otherwise specified. For example, $C_1$-$C_{10}$, as in "$C_1$-$C_{10}$ alkyl" is defined to include groups having 1, 2, 3, 4, 5, 6, 7, 8, 9 or 10 carbons in a linear, branched, or cyclic arrangement. For example, "$C_1$-$C_{10}$ alkyl" specifically includes methyl, ethyl, propyl, butyl, pentyl, hexyl, heptyl, octyl, nonyl, decyl, and so on.

"Alkoxy" or "alkyloxy" represents an alkyl group as defined above, unless otherwise indicated, wherein said alkyl group is attached through an oxygen bridge. Examples of alkoxy include methoxy, ethoxy and the like.

The term "cycloalkyl" or "carbocycle" shall mean cyclic rings of alkanes of three to eight total carbon atoms, unless otherwise indicated, or any number within this range (i.e., cyclopropyl, cyclobutyl, cydlopentyl, cyclohexyl, cycloheptyl or cyclooctyl).

If no number of carbon atoms is specified, the term "alkenyl" refers to a non-aromatic hydrocarbon radical, straight or branched, containing from 2 to 10 carbon atoms and at least 1 carbon to carbon double bond. Preferably 1 carbon to carbon double bond is present, and up to 4 non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated.

In certain instances, substituents may be defined with a range of carbons that includes zero, such as $(C_0-C_6)$alkylene-aryl. If aryl is taken to be phenyl, this definition would include phenyl itself as well as —$CH_2Ph$, —$CH_2CH_2Ph$, $CH(CH_3)$ $CH_2CH(CH_3)Ph$, and so on.

As used herein, "aryl" is intended to mean any stable monocyclic or bicyclic carbon ring of up to 12 atoms in each ring, wherein at least one ring is aromatic. Examples of such aryl elements include phenyl, naphthyl, tetrahydronaphthyl, indanyl, biphenyl, phenanthryl, anthryl or acenaphthyl. In cases where the aryl substituent is bicyclic and one ring is non-aromatic, it is understood that attachment is via the aromatic ring.

The term "heteroaryl", as used herein, represents a stable monocyclic, bicyclic or tricyclic ring of up to 10 atoms in each ring, wherein at least one ring is aromatic and contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, and tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

As appreciated by those of skill in the art, "halo" or "halogen" as used herein is intended to include chloro, fluoro, bromo and iodo. The term "keto" means carbonyl (C=O).

The term "haloalkyl" means an alkyl radical as defined above, unless otherwise specified, that is substituted with one to five, preferably one to three halogen. Representative examples include, but are not limited to trifluoromethyl, dichloroethyl, and the like.

The term "haloalkoxy" represents a radical —OR where R is alkyl as defined above that is substituted with one to five, preferably one to three halogen. Representative examples include, but are not limited to trifluoromethyloxy, dichloroethyloxy, and the like.

The term "arylalkyl" includes an alkyl portion where alkyl is as defined above and to include an aryl portion where aryl is as defined above. Examples of arylalkyl include, but are not limited to, benzyl, fluorobenzyl, chlorobenzyl, phenylethyl, phenylpropyl, fluorophenylethyl, and chlorophenylethyl. Examples of alkylaryl include, but are not limited to, toluyl, ethylphenyl, and propylphenyl.

The term "heteroarylalkyl" as used herein, shall refer to a system that includes a heteroaryl portion, where heteroaryl is as defined above, and contains an alkyl portion. Examples of heteroarylalkyl include, but are not limited to, thienylmethyl, thienylethyl, thienylpropyl, pyridylmethyl, pyridylethyl and imidazoylmethyl.

The term "cycloalkylalkyl" includes an alkyl portion where alkyl is as defined above and also includes an cycloalkyl portion where cycloalkyl is as defined above. Examples of cycloalkylalkyl include, but are not limited to, cyclopropylmethyl, cyclopentylmethyl, cyclohexylmethyl, cyclopropylethyl, and the like.

The term "heterocycloalkylalkyl" includes an alkyl portion where alkyl is as defined above and also includes a heterocycloalkyl portion where heterocycloalkyl is as defined above. Examples of heterocycloalkylalkyl include, but are not limited to, morpholinylmethyl, piperazinylmethyl, pyrrolidinylmethyl, and the like.

The term "hydroxyalkyl" means a linear monovalent hydrocarbon raidcal of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, and the like.

The term "heterocycle" or "heterocyclyl" as used herein is intended to mean a 5- to 10-membered nonaromatic ring, unless otherwise specified, containing from 1 to 4 heteroatoms selected from the group consisting of O, N, S, SO, or $SO_2$ and includes bicyclic groups. "Heterocyclyl" therefore includes, but is not limited to the following: piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also emcompassed by this definition.

The present invention also includes N-oxide derivatives and protected derivatives of compounds of Formula I. For example, when compounds of Formula I contain an oxidizable nitrogen atom, the nitrogen atom can be converted to an N-oxide by methods well known in the art. Also when compounds of Formula I contain groups such as hydroxy, carboxy, thiol or any group containing a nitrogen atom(s), these groups can be protected with a suitable protecting groups. A comprehensive list of suitable protective groups can be found in T. W. Greene, Protective Groups in Organic Synthesis, John Wiley & Sons, Inc. 1981, the disclosure of which is incorporated herein by reference in its entirety. The protected derivatives of compounds of Formula I can be prepared by methods well known in the art.

Whenever the term "alkyl" or "aryl" or either of their prefix roots appear in a name of a substituent (e.g., aryl $C_{0-8}$ alkyl) it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The pharmaceutically acceptable salts of the compounds of this invention include the conventional non-toxic salts of the compounds of this invention as formed inorganic or organic acids. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic and the like. The preparation of the pharmaceutically acceptable salts described above and other typical pharmaceutically acceptable salts is more fully described by Berg et al., "Pharmaceutical Salts," *J. Pharm. Sci.*, 1977:66:1-19, hereby incorporated by reference. The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

For purposes of this specification, the following abbreviations have the indicated meanings:

| | |
|---|---|
| Ba(OH)$_2$ = | barium hydroxide |
| BuLi = | butyl lithium |
| CDI = | carbonyl diimidazole |
| CrO$_3$ = | chromium oxide |
| DMF = | N,N-dimethylformamide |
| EDC = | Ethyldiethylaminopropylcarbodiimide |
| Et$_3$N = | triethylamine |
| EtOH = | ethanol |
| HATU = | o-(7-azabenzotriazol-1-yl)-N,N,N',N'-tetramethyluronium hexafluorophosphate |
| HCl = | hydrochloric acid |
| H$_5$IO$_6$= | periodic acid |
| KHMDS = | potassium hexamethyldisilazane |
| LDA = | lithium diisopropylamide |
| LiCl = | lithium chloride |
| MeOH = | methanol |
| NaBH$_4$ = | sodium borohydride |
| NaI = | sodium iodide |
| NaCNBH$_3$ = | sodium cyanoborohydride |
| Na$_2$CO$_3$ = | sodium carbonate |
| NaHCO$_3$ = | sodium hydrogencarbonate |
| NaOH = | sodium hydroxide |
| Na$_2$HPO$_4$ = | sodium dihydrogen phosphate |
| NaHSO$_3$= | sodium hydrogen sulfite |
| NH$_4$Cl = | ammonium chloride |
| Pd/C = | palladium on carbon |
| PdCl$_2$(dppf) = | [1,1'-bis(diphenylphosphino)ferrocene] dichloropalladium(II) |
| PG = | protecting group |
| iPr$_2$EtN = | diisopropylethylamine |
| PyBOP = | benzotriazol-1-yloxytris(pyrrolidino)phosphonium-hexafluorophosphate |
| rt = | room temperature |
| sat. aq. = | saturated aqueous |
| SiO$_2$ = | silica dioxide |
| THF = | tetrahydrofuran |
| TiCl$_4$ = | titanium(IV) chloride |
| tlc = | thin layer chromatography |
| Me = | methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |

The novel compounds of the present invention can be prepared according to the following general procedures using appropriate materials and are further exemplified by the following specific examples. The compounds illustrated in the examples are not, however, to be construed as forming the only genus that is considered as the invention. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

Schemes

Compounds of the present invention can be prepared according to Scheme 1, as indicated below. Thus an α-amino ester may be added to a haloalkyl ketone to form an aminal which may be dehydrated to an imine in the presence of a dehydrating agent such as TiCl$_4$, MgSO$_4$ or isopropyl trifluoroacetate. Reduction of the imine with a reducing agent such as sodium cyanoborohydride or sodium borohydride provides the amine. Alternatively, a chiral catalyst could be used in this reduction to generate the appropriate chirality at the R$^4$ stereocenter. Ester hydrolysis and amide formation with an appropriately substituted aminoacetonitrile provides the imide derivative. If the substituent on D system is a halogen, a palladium-catalyzed Suzuki coupling with an appropriate boronic acid provides additional compounds of the current invention.

SCHEME 1

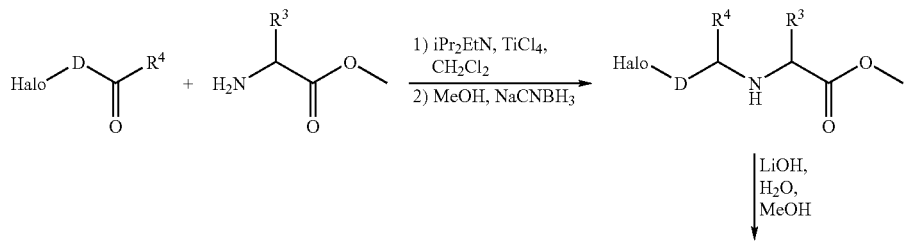

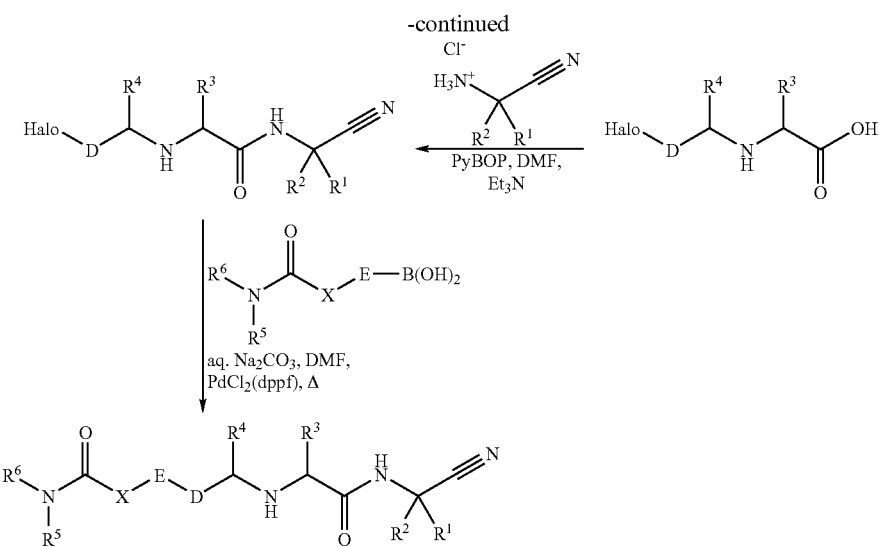

Compounds of the present invention may also be prepared according to Scheme 2, as indicated below. A ketone or aldehyde (or its hemiacetal) may be condensed with an amino alcohol to give a cyclic aminal. Treatment with 3 equivalents of a Grignard reagent or organolithium reagent will provide the appropriate alkylated amino alcohol. Oxidation of the alcohol with a chromium system such as a Jones oxidation or $H_5IO_6/CrO_3$, or alternatively by a two-step oxidation (eg oxalyl chloride/DMSO/Et$_3$N followed by NaClO) will provide the corresponding carboxylic acid. Peptide coupling and Suzuki reaction as described in Scheme 1 will provide compounds of the current invention.

SCHEME 2

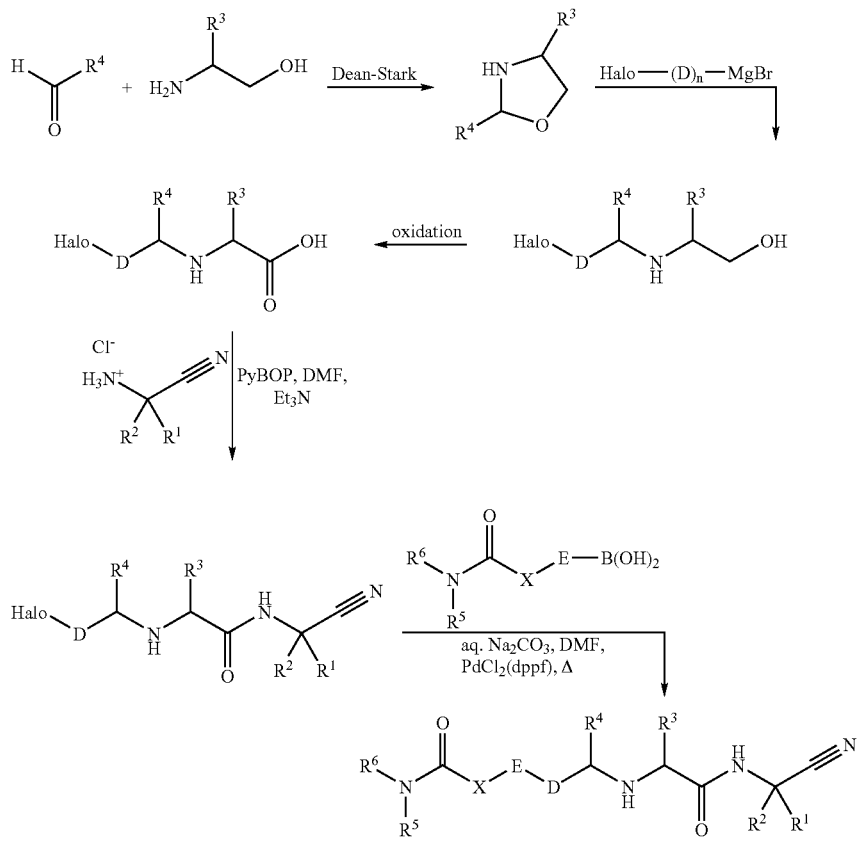

Compounds of the current invention may also be prepared according to Scheme 3, as indicated below. A hemiacetal may be condensed with an amino alcohol in which the alcohol moiety is protected with a suitable protecting group. Treatment of the resulting imine with a Grignard reagent or organolithium reagent will provide the appropriate alkylated amino alcohol. The alcohol protecting group can then be removed and the alcohol can be converted into compounds of the current invention either by the method described in Scheme 2 or by first conducting the Suzuki reaction, followed by oxidizing the alcohol with $H_5IO_6/CrO_3$ and then peptide coupling.

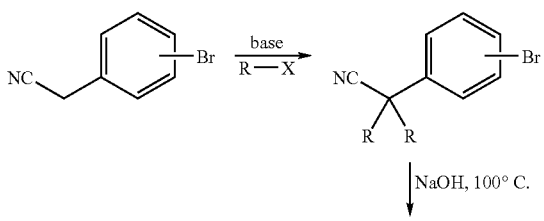

SCHEME 4

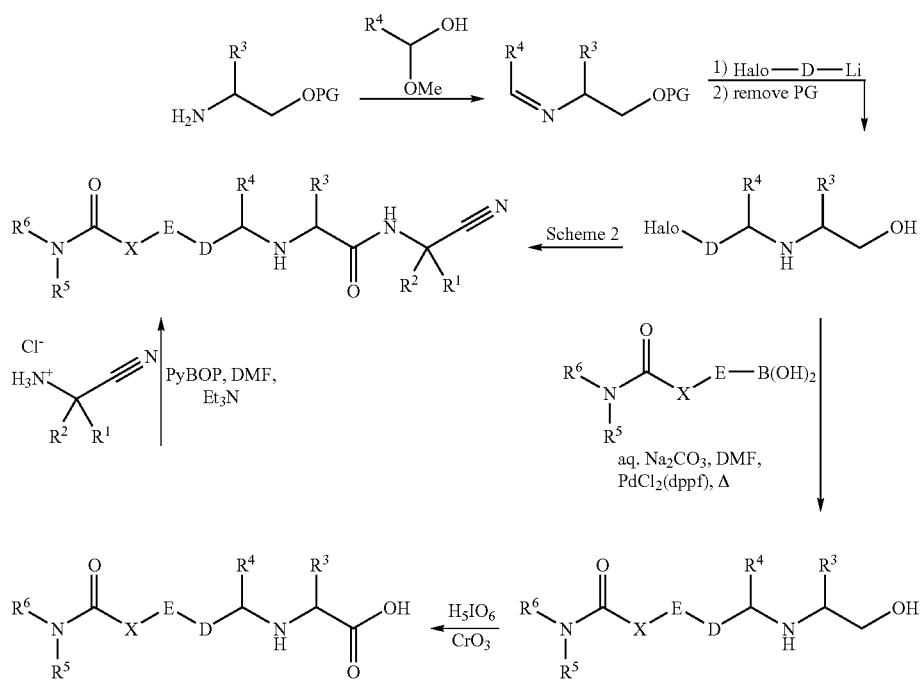

SCHEME 3

Carboxylamide-aryl bromides used to make compounds of the current invention may be prepared as shown in Scheme 4. Treatment of a bromophenylacetonitrile with a base such as LDA or KHMDS followed by treatment with an alkyl halide such as methyl iodide or 1-bromo-2-chloroethane gives alpha-substituted benzonitriles. Alternatively, this alkylation may be carried out under phase transfer conditions using sodium hydroxide, the alkyl halide and a suitable phase transfer catalyst such as benzyltriethylammonium chloride. Hydrolysis of the nitrile under basic conditions provides the corresponding carboxylic acid which can be coupled with ammonia or a primary or secondary amine using an appropriate coupling reagent such as EDC, CDI, HATU, pyBOP or isobutylchloroformate. This substituted aryl bromide may be coupled with an arylboron pinacolate as described in Scheme 8 to give compounds of the current invention. Alternatively, the aryl bromide may itself be converted into an arylboron pinacolate by a palladium-catalyzed reaction with bis(pinacolato)diboron. This resulting arylboron pinacolate may be used in the Suzuki coupling reactions shown in Schemes 1, 2, or 3 to provide compounds of the current invention.

-continued

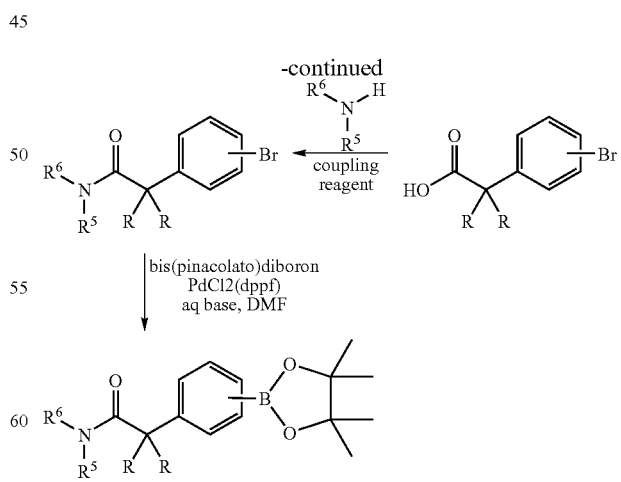

The 4-fluoroleucinol may be synthesized according to Scheme 5. 4,5-Dehydroleucine is converted to (4S)-4-(2-methylprop-2-enyl)-1,3-oxazolidin-2-one as described in the scheme below. This intermediate is then treated with a hydrofluorination reagent such as BF-pyridine to give (4S)-4-(2-fluoro-2-methylpropyl)-1,3-oxazolidin-2-one. Basic hydrolysis (i.e. Ba(OH)$_2$ or NaOH) then affords (2S)-2-amino-4-fluoro-4-methylpentan-1-ol, which may be used as shown in Scheme 2. Selective protection of the alcohol provides an intermediate that can be used in Scheme 3.

SCHEME 5

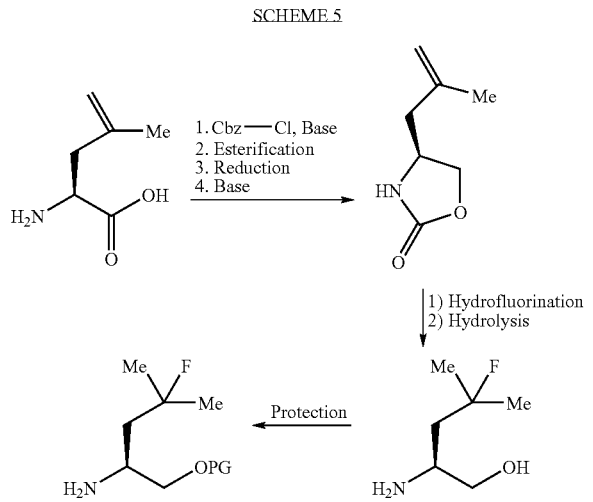

The amino alcohols used for the present invention may also be synthesized according to Scheme 6. A protected amino acid is reduced with a reducing agent such as NaBH$_4$ with or without an additive such as LiCl, in a solvent such as EtOH or a mixed solvent system such as EtOH/THF. The amino protecting group is then removed with the appropriate method according to the nature of the protecting group. The amino alcohol can then be silylated for use in Scheme 3. Alternatively, the alcohol may be silylated prior to deprotection of the amine, followed by removal of an orthogonal amine protecting group.

SCHEME 6

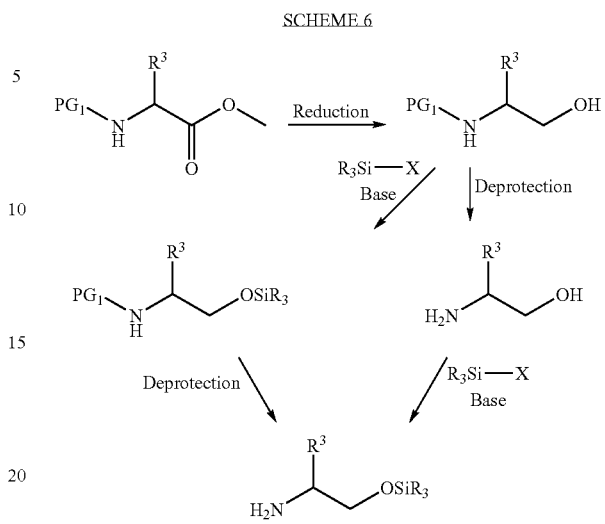

Compounds of the current invention may also be prepared according to Scheme 7, as shown below. Reaction of a suitably N-protected amino acid derivative with oxetane tosylate in the presence of sodium iodide in a suitable organic solvent such as dimethylformaamide provides the corresponding oxetane ester which upon treatment with diborane provides the ortho ester. Removal of the amino protecting group affords an amine which upon condensation with an aldehyde of formula R$^4$CHO or a hemiacetal of formula R$^4$C(OH)(OR) (where R is an alkyl group) under the reaction conditions described above provides an imine. Treatment of the imine with a Grignard or organolithium reagent under the reaction conditions described above provides an N-alkylated derivative. Removal of the ortho ester provides the corresponding carboxylic acid which is then converted into compounds of the current invention as described in Scheme 1.

SCHEME 7

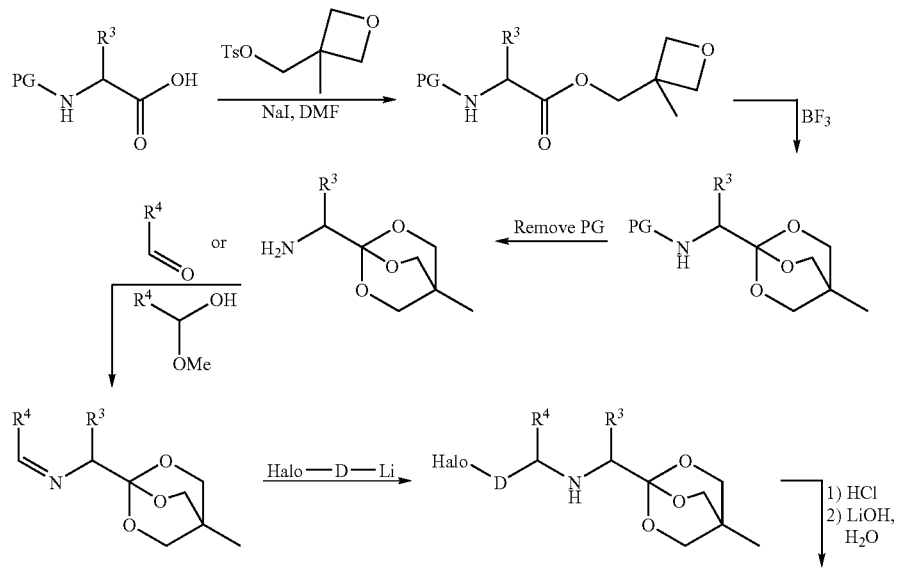

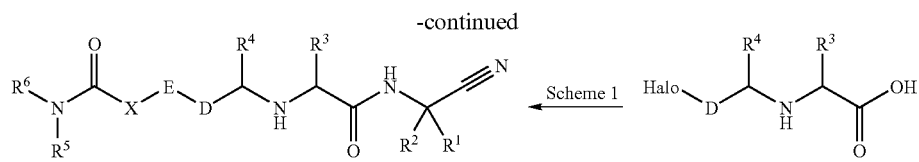

Compounds of the current invention may also be prepared as shown in Scheme 8. A aryl halide containing appropriate R¹, R², R³ and R⁴ groups may be coupled with bis(pinacolato) diboron to give the aryl pinacolate. This may be coupled with amide-containing arylbromides under Suzuki conditions to provide compounds of the current invention. Alternatively, this aryl pinacolate may be coupled with carboxylic acid-containing arylbromides under Suzuki conditions to provide an acid which may then be coupled with a suitable amine to provide compounds of the current invention.

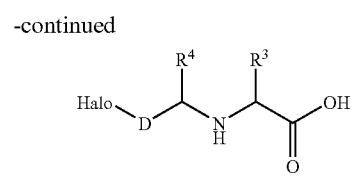

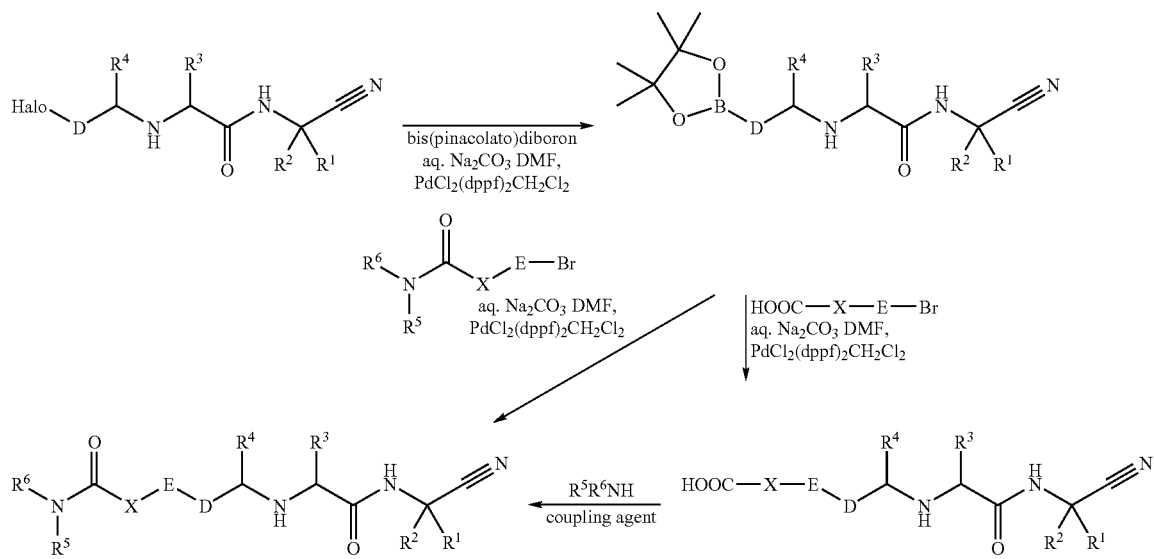

Carboxylic acids of the form Halo-D-CH(R⁴)NHCH(R³)COOH shown in Schemes 1, 2, and 7 may also be prepared as shown in Scheme 9. An appropriately substituted benzyl bromide, iodide or triflate (which may be chiral or racemic) may be coupled with an alpha amino ester under basic conditions. Hydrolysis with aqueous base then provides the acid which can be converted into examples of the current invention.

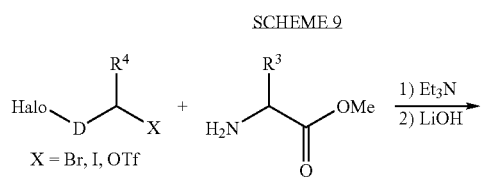

EXAMPLE 1

Synthesis of N¹-(1-cyanocyclopropyl)-N²-[(1S)-1-(4'-{1-[(cyclopropylamino)carbonyl]cyclopropyl}-2'-fluorobiphenyl-4-yl)-2,2,2-trifluoroethyl]-4-fluoro-L-leucinamide

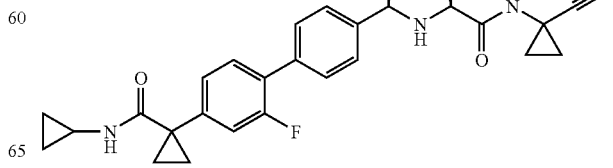

Step 1: Preparation of 1-bromo-4-(bromomethyl)-2-fluorobenzene

To a room temperature solution of 4-bromo-3-fluorotoluene (10.6 g) in 150 mL of carbon tetrachloride were added benzoyl peroxide (100 mg) and N-bromosuccinimide (10 g). The mixture was heated at 80° C. (with shine light) for 4 hours. The reaction mixture was cooled to 0° C. Filtered through celite, washed with hexanes and the solvent removed in vacuo. The crude material was purified by chromatography on $SiO_2$ using hexanes to yield the title compound containing ~30% of 1-bromo-4-(dibromomethyl)-2-fluorobenzene as impurity.

$^1$H NMR ($CD_3COCD_3$) δ 7.66-7.10(1H, m), 7.42(1H, d), 7.29(1H, d), 4.66(2H, s).

Step 2: Preparation of (4-bromo-3-fluorophenyl)methanol

To a room temperature solution of 1-bromo-4-(bromomethyl)-2-fluorobenzene from Step 1 (11.8 g) in DMF (150 mL) was added sodium acetate (10.8 g). The mixture was heated at 80° C. for 16 hours. It was cooled to room temperature and poured into ice and saturated aqueous sodium bicarbonate (200 mL), and extracted with diethyl ether (2×100 mL). The combined extracts were washed with brine, dried with magnesium sulfate and the solvent removed in vacuo. The crude material was purified by chromatography on $SiO_2$ using ethyl acetate and hexanes (1:25 to 1:10) to yield 4-bromo-3-fluorobenzyl acetate (containing about 15% of 4-bromo-3-fluorobenzaldehyde). The residue was dissolved in methanol (100 mL), cooled at 0° C. and sodium methoxide (250 mg) was added. The reaction mixture was stirred at room temperature for 2 hours. It was cooled to 0° C. and sodium borohydride was added (1.5 g). Stirred at 0° C. for 1 hour and poured into ice and saturated aqueous ammonium chloride (200 mL). Extracted with ethyl acetate (2×100 mL). The combined extracts were washed with brine, dried with magnesium sulfate and the solvent removed in vacuo. The residue was purified by chromatography on $SiO_2$ using ethyl acetate and hexanes (1:5 to 1:3) to yield the title compound.

$^1$H NMR ($CD_3COCD_3$) δ 7.55-7.65(1H, m), 7.28(1H, d), 7.15(1H, d), 4.63(2H, d), 4.50 (1H, t).

Step 3: Preparation of (4-bromo-3-fluorophenyl)acetonitrile

To a −78° C. solution of (4-bromo-3-fluorophenyl)methanol from Step 2 (7.2 g) and triethylamine (5.9 mL) in dichloromethane (300 mL) was slowly added methanesulphonyl chloride (3.0 mL). The reaction mixture was stirred at 0° C. for 1 hour. Then poured into ice and saturated aqueous ammonium chloride and partitioned. The aqueous layer was extracted with dichloromethane (1×150 mL). The combined extracts were washed with brine, dried with magnesium sulfate and the solvent removed in vacuo. The residue was dissolved in DMF (150 mL) and sodium cyanide (5.1 g) was added. The reaction mixture was stirred at room temperature for 2 hours and poured into ice and water (100 mL). Extracted with ethyl acetate (2×100 mL). The combined extracts were washed with brine, dried with magnesium sulfate and the solvent removed in vacuo. The residue was purified by chromatography on $SiO_2$ using ethyl acetate and hexanes (1:10 to 1:5) to yield the title compound.

$^1$H NMR ($CD_3COCD_3$) δ 7.70-7.78(1H, m), 7.39(1H, d), 7.28(1H, d), 4.09(2H, s).

Step 4: Preparation of 1-(4-bromo-3-fluorophenyl)cyclopropanecarbonitrile

To a room temperature solution of (4-bromo-3-fluorophenyl)acetonitrile from Step 3 (6.4 g) in a solution of 7.5 mL of sodium hydroxide (50% in water W/W) were added 1-bromo-2-chloroethane (4.0 mL) and benzyltriethylammonium chloride (204 mg). The mixture was heated at 60° C. for 5 hours. The reaction mixture was cooled to room temperature and poured into water (100 mL). Extracted with ethyl acetate (200 mL). The extracts were washed with water (100 mL), hydrogen chloride (100 mL, 10% HCl in water) and brine. Then dried with magnesium sulfate and the solvent removed in vacuo. The residue was purified by swish using methyl t-butyl ether and hexanes to yield the title compound.

$^1$H NMR ($CD_3COCD_3$) δ 7.69-7.73(1H, m), 7.28(1H, d), 7.25(1H, d), 1.80-1.87(2H, m), 1.59-1.65(2H, m).

Step 5: Preparation of 1-(4-bromo-3-fluorophenyl)cyclopropanecarboxylic acid

To a room temperature solution of 1-(4-bromo-3-fluorophenyl)cyclopropanecarbonitrile from Step 4 (4.3 g) in ethyl alcohol (40 mL) was added a solution of 20 mL of sodium hydroxide (25% NaOH in water W/W). The mixture was heated at 100° C. overnight. It was cooled to room temperature and poured into ice and hydrogen chloride (1 N), and extracted with dichloromethane (2×100 mL). The combined extracts were washed with brine, dried with magnesium sulfate and the solvent removed in vacuo. The residue was purified by swish using methyl t-butyl ether and hexanes to yield the title compound.

$^1$H NMR ($CD_3COCD_3$) δ 10.75-10.98(1H, bs), 7.59-7.65 (1H, m), 7.35(1H, d), 7.22(1H, d), 1.58-1.65(2H, m), 1.25-1.32(2H, m).

Step 6: Preparation of 1-(4-bromo-3-fluorophenyl)-N-cyclopropylcyclopropanecarboxamide To a 0° C. solution of 1-(4-bromo-3-fluorophenyl)cyclopropanecarboxylic acid from Step 5 (2.0 g) in DMF (20 mL) was added O-(7-azabenzotriazol-1-yl)-N,N,N',N'-tetramethyluronium hexafluorophosphate (3.5 g) and cyclopropylamine (1.15 mL). After stirring for 1 min, diisopropylethylamine (4.3 mL) was added dropwise and the mixture was stirred at room temperature for 16 hours. The resultant mixture was poured into saturated aqueous sodium bicarbonate and extracted with ethyl acetate (3×50 mL). The combined extracts were washed with brine, dried with magnesium sulfate and the solvent removed in vacuo. The residue was purified by chromatography on $SiO_2$ using hexanes and ethyl acetate (1:2 to 1:1) to afford the title compound.

$^1$H NMR ($CD_3COCD_3$) δ 7.59-7.65(1H, m), 7.30(1H, d), 7.20(1H, d), 6.44(1H, bs), 1.44-1.51(2H, m), 1.00-1.09(2H, m), 0.50-0.60(2H, m), 0.30-0.40(2H, m).

Step 7: Preparation of benzyl (3S)-3-[(tert-butoxycarbonyl)amino]-4-hydroxubutanoate N-(tert-Butoxycarbonyl)-L-aspartic acid 4-benzyl ester (30 g) was dissolved in dimethoxyethane (90 mL) and the solution was cooled to −5° C. N-Methylmorpholine (10.32 mL) was added followed by a slow addition of isobutyl chloroformate (12.66 mL) such that the reaction temperature was kept below −10° C. The mixture was aged for 0.5 hour. The solids were quickly filtered and washed with dimethoxyethane (90 mL). The filtrate was cooled to −50° C. and a solution of sodium borohydride (4.4 g) in water (45 mL) was added slowly such that the reaction temperature was maintained between −30° C. and −15° C. Water (500 mL) was then added such that the reaction mixture temperature was maintained below −15° C. The suspension was filtered, the solid washed with water (400 mL) and dried to yield benzyl (3S)-3-[(tert-butoxycarbonyl)amino]-4-hydroxybutanoate.

$^1$H NMR ($CD_3COCD_3$) δ 7.3-7.45 (5H, m), 5.85-5.95 (1H, NH), 5.15 (2H, s), 3.95-4.1 (2H, m), 3.5-3.7 (2H, m), 2.55-2.75 (2H, m), 1.4 (9H, s).

Step 8: Preparation of benzyl [(4S)-2-oxo-1,3-oxazolidin-4-yl]acetate

To a solution of the alcohol (95.7 g) from Step 7 in dichloroethane (925 mL) was added pyridine (625 mL) and the mixture was cooled to 0-5° C. Anhydrous p-toluenesulfonic anhydride (105.7 g) was added and the mixture was warmed to room temperature and stirred for 1 hour and then heated to 90° C. for 2 hours. The mixture was cooled, diluted with dichloromethane (1000 mL) and washed with 1N HCl (3×600 mL). The organic layer was washed with brine, dried with sodium sulfate and the solvents were removed in vacuo. The residue was purified by chromatography on $SiO_2$ using ethyl acetate and hexanes in a 1:1 ratio followed by ethyl acetate to yield benzyl [(4S)-2-oxo-1,3-oxazolidin-4-yl]acetate.

$^1$H NMR ($CD_3SOCD_3$) δ 7.8 (1H, NH), 7.3-7.45 (5H, m), 5.05-5.15 (2H, m), 4.4-4.5 (1H, m), 4.1-4.2 (1H, m), 4.0-4.05 (1H, m), 3.6-3.8 (2H, m).

Step 9: Preparation of (4S)-4-(2-hydroxy-2-methylpropyl)-1,3-oxazolidin-2-one

Methylmagnesium bromide (227 mL of 3M solution in diethyl ether) was added to a mixture of toluene (340 mL) and THF (340 mL) at −20° C. A warm THF solution (170 mL) of the ester from Step 8 (40 g) was then added dropwise maintaining the temperature below −10° C. The mixture was aged for 2 hours and was then slowly added to a mixture of water (1000 mL) and acetic acid (200 mL) and the resultant mixture was stirred for 2 hours at room temperature. The aqueous layer was separated and the organic layer was extracted with water (2×200 mL). The product was extracted from the combined aqueous layers using dichloromethane and a continuous extractor. The dichloromethane extract was evaporated to dryness using heptane as a co-solvent to azeotrope off the acetic acid. The residue was purified by chromatography on $SiO_2$ using ethanol and dichloromethane (1:30) to yield (4S)-4-(2-hydroxy-2-methylpropyl)-1,3-oxazolidin-2-one.

$^1$H NMR ($CD_3COCD_3$) δ 6.1-6.4 (1H, NH), 4.45-4.55 (1H, m), 4.1-4.2 (1H, m), 3.95-4.05 (1H, m), 3.7 (1H, s), 1.65-1.85 (2H, m), 1.25 (6H, m).

Step 10: Preparation of (4S)-4-(2-fluoro-2-methylpropyl)-1,3-oxazolidin-2-one

A dichloromethane solution (100 mL) of the alcohol (47.8 g) from Step 9 was added to a −70° C. solution of (diethylamino)sulfur trifluoride (48.5 g) in dichloromethane (500 mL). The mixture was warmed to room temperature and stirred for 1 hour. The mixture was then carefully added to a 0° C. mixture of saturated aqueous $NaHCO_3$ (800 mL). The organic layer was separated and washed with saturated aqueous $NaHCO_3$. The aqueous was further extracted with dichloromethane (100 mL) and the combined dichloromethane layers were dried and concentrated. The residue was purified by chromatography on $SiO_2$ using ethyl acetate and hexanes (1:5) followed by ethyl acetate to yield (4S)-4-(2-fluoro-2-methylpropyl)-1,3-oxazolidin-2-one.

$^1$H NMR ($CD_3SOCD_3$) δ 7.6 (1H, NH), 4.4-4.5 (1H, m), 3.95-4.05 (1H, m), 3.9-3.95 (1H, m), 1.8-1.95 (2H, m), 1.25-1.4 (6H, 2s).

Step 11: Preparation of (2S)-2-amino-4-fluoro-4-methylpentan-1-ol

To a solution of the fluoro derivative (21.0 g) from Step 10 in 90% aqueous ethyl alcohol (216 mL) was added potassium hydroxide (21.9 g). The mixture was heated at reflux for 4 hours and cooled to room temperature. The mixture was then concentrated and co-evaporated with toluene (3×300 mL). The residue was dissolved in dichloromethane (500 mL) and stirred for 0.5 hour. The suspension was filtered through celite and the celite was washed with dichloromethane (3×100 mL). The filtrate was concentrated to dryness to yield (2S)-2-amino-4-fluoro-4-methylpentan-1-ol.

$^1$H NMR ($CD_3OD$) δ 3.4-3.5 (1H, m), 3.2-3.3 (1H, m), 3.0-3.1 (1H, m), 1.5-1.7 (2H, m), 1.35 (3H, s), 1.3 (3H, s).

Step 12: Preparation of (2S)-1-{[tert-butyl(dimethyl)silyl]oxy}-4-fluoro-4-methylpentan-2-amine The amino alcohol (21.0 g) from Step 11 was dissolved in dichloromethane (300 mL) and the solution was cooled to 0° C. 4-(dimethylamino) pyridine (0.051 g) and tert-butyldimethylsilyl chloride (21 g) were added followed by triethylamine (25 mL). The mixture was stirred at room temperature overnight. The reaction mixture was slowly poured into 0° C. saturated aqueous ammonium chloride and extracted with dichloromethane (3×300 mL). The organic layer was washed with brine, dried with sodium sulfate and the solvents were removed in vacuo to yield (2S)-1-{[tert-butyl(dimethyl)silyl]oxy}-4-fluoro-4-methylpentan-2-amine.

$^1$H NMR ($CD_3OD$) δ 3.6-3.65 (1H, m), 3.4-3.5 (1H, m), 3.1-3.2 (1H, m), 1.6-1.8 (2H, m), 1.35-1.45 (6H, m), 0.93 (9H, s), 0.1 (6H, s).

Step 13: Preparation of (2S)-1-{[tert-butyl(dimethyl)silyl]oxy}-4-fluoro-4-methyl-N-[(1E)-2,2,2-trifluoroethylidene]pentan-2-amine To a solution of the amine (31.5 g) from Step 12 in benzene (126 mL) was added trifluoroacetaldehyde methyl hemiacetal (21.6 mL.). The solution was heated at reflux overnight using a Dean-Stark trap to collect water. The reaction mixture was cooled to room temperature and concentrated to dryness. The residue was purified on $SiO_2$ using 4% of ethyl acetate in hexanes to yield (2S)-1-{[tert-butyl(dimethyl)silyl]oxy}-4-fluoro-4-methylpentan-2-amine.

$^1$H NMR ($CD_3COCD_3$) δ 7.9-7.95 (1H, m), 3.75-3.85 (1H, m), 3.7-3.75 (1H, m), 3.53-3.6 (1H, m), 1.9-2.0(2H, m), 1.3-1.4 (6H, m), 0.9 (9H, (3H, s), 0.05 (3H, s).

Step 14: Preparation of (2S)-2-{[(1S)-1-(4-bromophenyl)-2,2,2-trifluoroethyl]amino}-4-fluoro-4-methylpentan-1-ol To a −75° C. solution of 1,4-dibromobenzene (0.26 g) in THF (4 mL) was added n-BuLi (0.42 mL of a 2.5M hexanes solution) and the mixture was aged for 20 minutes. The imine (0.329 g) from Step 13 in THF (2 mL) was added and the mixture was aged 2 hours. The mixture was then added to a mixture of water (50 mL), $NH_4Cl$ (1 g) and crushed ice. It was extracted with ethyl acetate (2×25 mL) and the combined ethyl acetate layers were dried and evaporated to dryness.

The same procedure was repeated on a larger scale using 1,4-dibromobenzene (1.2 g), n-BuLi (1.84 mL) and the imine (1.38 g) and the reaction mixture was treated as above. The combined residues from both preparations were dissolved in THF (10 mL) and cooled to 0° C. n-Tetrabutylammonium fluroride (6 mL from a 1M THF solution) was added and the mixture was stirred at +5° C. for 16 h. The mixture was poured into a mixture of water (50 mL), ammonium chloride (1 g) and crushed ice and the organic layer was separated. The aqueous was further extracted with ethyl acetate (2×15 mL) and the combined organic layers were dried and concentrated. The residue was purified on $SiO_2$ using ethyl acetate and hexanes (1:5) to yield (2S)-2-{[(1S)-1-(4-bromophenyl)-2,2,2-trifluoroethyl]amino}-4-fluoro-4-methylpentan-1-ol.

$^1$H NMR ($CD_3COCD_3$) δ 7.65 (2H, m), 7.5 (2H, m), 4.5-4.6 (1H, m), 3.8 (1H, m), 3.6 (1H, m), 3.3-3.4 (1H, m), 2.85-2.0 (1H, m), 2.55 (1H, m), 1.7-1.9 (2H, s), 1.3-1.4 (6H, m).

Step 15: Preparation $N^2$-[(1S)-1-(4-bromophenyl)-2,2,2-trifluoroethyl]-$N^1$-(1-cycanocyclopropyl)-4-fluoro-L-leucinamide A suspension of $H_5IO_6/CrO_3$ (66 mL of 0.44 M in $CH_3CN$; Note) was cooled to 0° C. and a solution of the alcohol from Step 14 (1.55 g) in $CH_3CN$ (5 mL) was added dropwise. The mixture was stirred at 0-5° C. for 3.5 hours. It was poured into pH 4 $Na_2HPO_4$ (200 mL) under vigorous stirring and the mixture was extracted with diethyl ether (3×50 mL). The combined ether extracts were washed with water and brine (1:1) followed by dilute aqueous NaHSO₃ and brine. The mixture was dried with sodium sulfate, filtered and the solvents were evaporated to dryness to yield of N-[(1S)-1-(4-bromophenyl)-2,2,2-trifluoroethyl]-4-fluoro-L-leucine which was used as such in the next step.

Note. The oxidizing reagent (H₅IO₆/CrO₃) was prepared as described in Tetrahedron Letters 39 (1998) 5323-5326 but using HPLC grade CH₃CN (contains 0.5% water); no water was added.

Diisopropylethylamine (4.2 mL) was added to a 0° C. suspension of the acid (1.5 g) from above, 1-amino-1-cyclopropanecarbonitrile hydrochloride (1.18 g), O-(7-azabenzotriazol-1-yl)-N,N,N',N'-tetramethyluronium hexafluorophosphate (1.94 g) and dimethylformamide (5 mL) and the mixture was reacted at room temperature for 48 h. It was then poured on ice and dilute aqueous ammonium chloride. The mixture was extracted with ethyl acetate and ether (1:1) and the combined organic layers were washed with pH 3 dilute Na₂HPO₄ and brine. The solvents were evaporated to dryness and the residue was purified by chromatography on SiO₂ using ethyl acetate and hexanes (1:2) to yield N²-[(1S)-1-(4-bromophenyl)-2,2,2-trifluoroethyl]-N¹-(1-cyanocyclopropyl)-4-fluoro-L-leucinamide in a sufficient purity state for the next step.

¹H NMR (CD₃COCD₃) δ 8.15 (1H, NH), 7.6 (2H, m), 7.45 (2H, m), 4.35-4.45 (1H, m), 3.45-3.55 (1H, m), 1.9-2.1 (2H, m), 1.75-1.85 (1H, NH),1.35-1.55 (8H, m), 1.1-1.15 (1H, m), 0.95-1.05 (1H, m).

Step 16: N¹-(1-cyanocyclopropyl)-4-fluoro-N²-{(1S)-2,2,2-trifluoro-1-[4-(4,4,5,5-tetramethyl-1,3,2-dioxaborolan-2-yl)phenyl]ethyl}-L-leucinamide A stream of nitrogen was passed through a DMF (40 mL) suspension of N²-[(1S)-1-(4-bromophenyl)-2,2,2-trifluoroethyl]-N¹-(1-cyanocyclopropyl)-4-fluoro-L-leucinamide from Step 15 (2.0 g), bis(pinacolato)diboron (1.24 g) and potassium acetate (1.53 g) for 15 minutes. The catalyst [1,1'-bis(diphenylphosphino)-ferrocene]dichloropalladium(II), complex (1:1) with dichloromethane (181 mg) was then added and the mixture warmed to 65° C. overnight under nitrogen. The mixture was cooled to room temperature, diluted with ethyl acetate and hexanes (1:1, 100 mL) and poured over water (50 mL) and ice (50 g). The organic layer was separated and the aqueous layer further extracted with ethyl acetate and hexanes (1:1, 3×50 mL). The combined extracts were washed with brine and dried with magnesium sulfate. Removal of the solvent left a residue which was purified by chromatography on SiO₂ using ethyl acetate and hexanes (1:3 to 1:2) to yield the title compound.

¹H NMR (CD₃COCD₃) δ 8.15(1H, bs), 7.78(2H, d), 7.50 (2H, d), 4.31-4.40 (1H, m), 3.47-3.54 (1H, m), 2.72-2.80 (2H, m), 1.32-1.48(9H, m), 1.05-1.11(1H, m), 0.87-0.95(1H, m).

Step 17: Preparation of N¹-(1-cyanocyclopropyl)-N²-[(1S)-1-(4-{1-[(cyclopropylamino)carbonyl]cyclopyl}-2'-fluoro-biphenyl-4-yl)-2,2,2-trifluoroethyl]-4-fluoro-L-leucinamide A stream of nitrogen was passed through a solution of DM (4 mL), N¹-(1-cyanocyclopropyl)-4-fluoro-N²-{(1S)-2,2,2-trifluoro-1-[4-(4,4,5,5-tetramethyl-1,3,2-dioxaborolan-2-yl)phenyl]ethyl}-L-leucinamide from Step 15 (350 mg), 1-(4-bromo-3-fluorophenyl)-N-cyclopropylcyclopropane carboxamide from Step 6 (250 mg) and 2 M Na₂CO₃ (900 µL) for 15 minutes followed by the addition of [1,1'-bis(diphenylphosphino)-ferrocene]dichloropalladium(II), complex (1:1) with dichloromethane (29 mg). The mixture was warmed to 80° C. for 3 hours under nitrogen. The mixture was cooled to room temperature, poured into ice (20 g) and saturated aqueous sodium bicarbonate (20 mL) and extracted with ethyl acetate (3×60 mL). The combined extracts were washed with brine and dried with magnesium sulfate. Removal of the solvent left a residue that was purified by chromatography on SiO₂ using ethyl acetate and hexanes (1:1 to 2:1) as eluants, followed by a re-crystallization using isopropyl acetate and hexanes to yield the title compound.

¹H NMR (CD₃COCD₃) δ 8.18(1H, s), 7.60-7.70(4H, m), 7.50-7.55(1H, m), 7.33(1H, d), 7.28(1H, d), 6.40(1H, bs), 4.38-4.48(1H, m), 3.56 (1H, t), 2.67-2.69 (1H, m), 1.92-2.0 (2H, m), 1.45-1.46(10H, m), 1.05-1.11 (3H, m), 0.92-0.99 (1H, m), 0.56-0.60(2H, m), 0.36-0.38(2H, m).

EXAMPLE 2

Synthesis of N²-[(1S)-1-(4-{5-[1-(aminocarbonyl)cyclopropyl]pyridin-2-yl}phenyl)-2,2,2-trifluoroethyl]-N¹-(1-cyanocyclopropyl)-4-fluoro-L-leucinamide

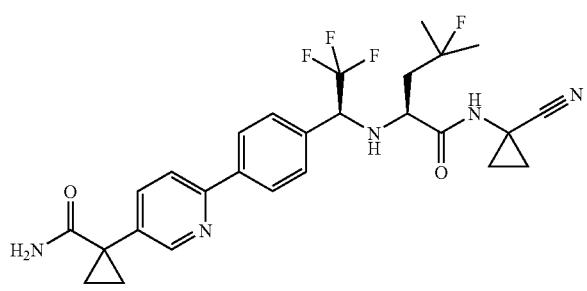

Step 1: Preparation of (6-chloropyridin-3-yl)methanol

To a –78° C. solution of ethyl 6-chloronicotinate (10 g) in 250 mL of THF was slowly added 126 mL of lithium aluminium hydride (1.5 M in toluene). The mixture was stirred at 0° C. for 1 hour. Poured into saturated aqueous tartaric acid (200 mL) and extracted with ethyl acetate (2×200 mL). The combined extracts were washed with brine, dried with magnesium sulfate and the solvent removed in vacuo. The residue was purified by chromatography on SiO₂ using ethyl acetate and hexanes (1:2 to 1:1) to yield the title compound.

¹H NMR (CD₃COCD₃) δ 8.35(1H, s), 7.80(1H, d), 7.40 (1H, d), 4.68(2H, d), 4.55(1H, t).

Step 2: Preparation of (6-chloropyridin-3-yl)acetonitrile

To a –78° C. solution of (6-chloropyridin-3-yl)methanol from Step 1 (7.5 g) and triethylamine (8.7 mL) in dichloromethane (250 mL) was slowly added methanesulphonyl chloride (4.5 mL). The reaction mixture was stirred at 0° C. for 1 hour. Then poured into ice and HCl (1N), adjusted pH at 4 with saturated aqueous disodium hydrogen phosphate and partitioned. The aqueous layer was extracted with dichloromethane (1×150 mL). The combined extracts were washed with brine, dried with magnesium sulfate and the solvent removed in vacuo. The residue was dissolved in DMF (100 mL) and sodium cyanide (2.8 g) was added. The reaction mixture was stirred at room temperature for 3 hours and poured into ice and water (100 mL). Extracted with ethyl acetate (2×100 mL). The combined extracts were washed with brine, dried with magnesium sulfate and the solvent removed in vacuo. The residue was purified by chromatography on SiO₂ using ethyl acetate and hexanes (1:5 to 1:2) to yield the title compound.

$^1$H NMR (CD$_3$COCD$_3$) δ 18.45(1H, s), 7.90(1H, d), 7.50 (1H, d), 4.06(2H, s).

Step 3: Preparation of 1-(6-chloropyridin-3-yl)cyclopropanecarbonitrile

To a room temperature solution of (6-chloropyridin-3-yl) acetonitrile from Step 2 (6.1 g) in a solution of 9.9 mL of sodium hydroxide (50% in water W/W) were added 1-bromo-2-chloroethane (5.3 mL) and benzyltriethylammonium chloride (273 mg). The mixture was heated at 60° C. overnight. The reaction mixture was cooled to room temperature, poured into water (100 mL) and extracted with ethyl acetate (200 mL). The extracts were washed with saturated aqueous ammonium chloride and brine. Then dried with magnesium sulfate and the solvent removed in vacuo. The residue was purified by swish using diethyl ether and hexanes to yield the title compound.

$^1$H NMR (CD$_3$COCD$_3$) δ 8.45(1H, s), 7.80(1H, d), 7.48 (1H, d), 1.80-1.87(2H, m), 1.59-1.68(2H, m).

Step 4: Preparation of 1-(6-chloropyridin-3-yl)cyclopropanecarboxylic acid

To a room temperature solution of 1-(6-chloropyridin-3-yl)cyclopropanecarbonitrile from Step 3 (5.3 g) in ethyl alcohol (60 mL) was added a solution of 30 mL of sodium hydroxide (25% NaOH w/w in water). The mixture was heated at 100° C. for 8 hours. It was cooled to room temperature and poured into saturated aqueous disodium hydrogen phosphate (at 0° C.) and an adjusted pH at 4 with hydrogen chloride (1 N). The mixture was extracted with dichloromethane (2×100 mL) and the combined extracts were washed with brine, dried with magnesium sulfate and the solvent was removed in vacuo. The residue was purified by swish using diethyl ether and hexanes to yield the title compound.

$^1$H NMR (CD$_3$COCD$_3$) δ 10.90(1H, bs), 8.44(1H, s), 7.88 (1H, d), 7.41(1H, d), 1.60-1.68(2H, m), 1.28-1.35(2H, m).

Step 5: Preparation of 1-(6-chloropyridin-3-yl)cyclopropanecarboxamide

To a 0° C. solution of 1-(6-chloropyridin-3-yl)cyclopropanecarboxylic from Step 4 (1.0 g) in chloroform (50 mL) were slowly added isobutyl chloroformate (800 μL) and triethylamine (920 μL). The reaction mixture was stirred at 0° C. for 2 hours. Then it was saturated with ammonia gas and stirred at 0° C. for 10 minutes. The reaction mixture was allowed to stand at room temperature for 1 hour then poured into water (80 mL) and partitioned. The aqueous layer was extracted with dichloromethane (2×80 mL). The combined extracts were washed with brine, dried with magnesium sulfate and the solvent removed in vacuo. The residue was purified by swish using diethyl ether and hexanes to yield the title compound.

$^1$H NMR (CD$_3$COCD$_3$) δ 8.40(1H, s), 7.83(1H, d), 7.40 (1H, d), 6.50(1H, bs), 6.29(1H, bs), 1.45-1.50(2H, m), 1.00-1.08(2H, m).

Step 6: Preparation of of N$^2$-[(1S)-1-(4-{5-[1-(aminocarbonyl)cyclopropyl]pyridin-2-yl}phenyl)-2,2,2-trifluoroethyl]-N$^1$-(1-cyanocyclopropyl)-4-fluoro-L-leucinamide A stream of nitrogen was passed through a solution of DMF/1-propanol (1 mL, 4 mL respectively), N$^1$-(1-cyanocyclopropyl)-4-fluoro-N$^2$-{(1S)-2,2,2-trifluoro-1-[4-(4,4,5,5-tetramethyl-1,3,2-dioxaborolan-2-yl)phenyl]ethyl}-L-leucinamide from Example 1, Step 15, (150 mg), 1-(6-chloropyridin-3-yl)cyclopropanecarboxamide from Step 5 (74 mg) and 2 M Na$_2$CO$_3$ (400 μL) for 15 minutes followed by the addition of palladium acetate (II), complex (4:1) with triphenylphosphine (16 mg). The mixture was warmed to 80° C. for 8 hours under nitrogen. The mixture was cooled to room temperature, poured into ice (20 g) and saturated aqueous sodium bicarbonate (20 mL) and extracted with ethyl acetate (3×60 mL). The combined extracts were washed with brine and dried with magnesium sulfate. Removal of the solvent left a residue that was purified by chromatography on SiO$_2$ (Combiflash) using ethyl acetate and hexanes (60% for 10 minutes, then 60 to 100% for 30 minutes) as eluants, followed by a swish using diethyl ether and hexanes to yield the title compound.

$^1$H NMR (CD$_3$COCD$_3$) δ 8.75(1H, s), 8.18-8.21 (3H, m), 7.95(1H, d), 7.91(1H, d), 7.60-7.62(2H, m), 6.40(1H, bs) 6.20(1H, bs), 4.38-4.48(1H, m), 3.50-3.60 (1H, m), 1.92-2.01 (2H, m), 1.35-1.52(10H, m), 1.09-1.17(3H, m), 0.92-1.02 (1H, m).

EXAMPLE 3

Synthesis of N$^2$-((1S)-1-{4'-[1-(aminocarbonyl)cyclopropyl]biphenyl-4-yl}-2,2-difluoroethyl)-N$^1$-(1-cyanocyclopropyl)-4-fluoro-L-leucinamide

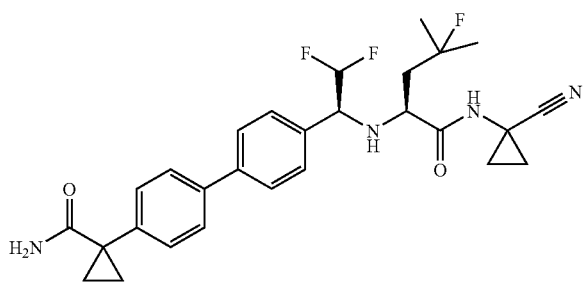

Step 1: Preparation of 1-(4-bromophenyl)cyclopropanecarbonitrile

To a room temperature solution of 4-bromophenylacetonitrile (18.0 g) in a solution of 22 mL of sodium hydroxide (50% in water W/W) were added 1-bromo-2-chloroethane and (2.0 mL) and benzyltriethylammonium chloride (627 mg). The mixture was heated at 60° C. overnight. The reaction mixture was cooled to room temperature and diethyl ether was added (300 mL) and partitioned. The ether layer was washed with water (100 mL), hydrogen chloride (100 mL, 10% HCl in water) and brine. Then dried with magnesium sulfate and the solvent removed in vacuo. The residue was purified by swish using diethyl ether and hexanes to yield the title compound.

$^1$H NMR (CD$_3$COCD$_3$) δ 7.60(2H, d), 7.35(2H, d), 1.74-1.80(2H, m), 1.52-1.57(2H, m).

Step 2: Preparation of 1-(4-bromophenyl)cyclopropanecarboxylic acid

To a room temperature solution of 1-(4-bromophenyl)cyclopropanecarbonitrile from Step 1 (13 g) in ethyl alcohol (110 mL) was added a solution of 56 mL of sodium hydroxide (25% NaOH in water W/W). The mixture was heated at 100° C. overnight. It was cooled to room temperature and poured into ice and hydrogen chloride (1 N), and extracted with dichloromethane (2×100 mL). The combined extracts were washed with brine, dried with magnesium sulfate and the solvent removed in vacuo to yield the title compound.

$^1$H NMR (CD$_3$COCD$_3$) δ 7.50(2H, d), 7.35(2H, d), 1.53-1.60(2H, m), 1.18-1.22(2H, m).

Step 3: Preparation of 1-(4-bromophenyl)cyclopropanecarboxamide

To a −15° C. solution of 1-(4-bromophenyl)cyclopropanecarboxylic acid from Step 2 (1.5 g) in chloroform (60 mL) were slowly added isobutyl chloroformate (900 μL) and triethylamine (1.1 mL). The reaction mixture was stirred at −15°

C. for 2 hours. Then it was saturated with ammonia gas and stirred at −15° C. for 10 minutes. The reaction mixture was allowed to stand at room temperature for 1 hour then poured into water (60 mL) and partitioned. The aqueous layer was extracted with dichloromethane (2×160 mL). The combined extracts were washed with brine, dried with magnesium sulfate and the solvent removed in vacuo. The residue was purified by swish using diethyl ether and hexanes to yield the title compound.

$^1$H NMR (CD$_3$COCD$_3$) δ 7.54(2H, d), 7.40(2H, d), 6.45 (1H, bs), 5.96(1H, bs), 1.42-1.48(2H, m), 0.98-1.02(2H, m).

Step 4: Preparation of 1-[4-(4,4,5,5-tetramethyl-1,3,2-dioxaborolan-2-yl)phenyl]cyclopropanecarboxamide.

1-(4-bromophenyl)cyclopropanecarboxamide from Step 3 (14.2 g, 59.2 mmol), bis-(pinacolato)diboron (18.0 g, 70.9 mmol, 1.2 equiv) and potassium acetate (20.4 g, 208 mmol, 3.5 equiv) were mixed in N,N-dimethylformamide (300 mL). The mixture was degassed 3 times with nitrogen, then [1,1'-bis(diphenylphosphino)ferrocene]palladium (II) chloride, 1:1 com-plex with dichloromethane (2.16 g, 3.0 mmol, 0.05 equiv) was added and the mixture was degassed again 3 times with nitrogen. The reaction mixture was heated at 65° C. for 18 hours, then poured into H$_2$O (1.2 L), and extracted with ethyl acetate (2×300 mL). The combined organic fractions were washed with brine, dried over sodium sulfate and evaporated to dryness. The brown residue was passed through a small pad of silica with ethyl acetate/hexanes (2:1) as eluant. The recovered light yellow solid was stirred in 20% ethyl acetate/hexanes (250 mL) for 6 hours, then filtered to give the title compound.

$^1$H NMR (500 MHz, acetone d$_6$) δ 7.7 (d, 2H), 7.45 (d, 2H), 6.4 (s, br, 1H), 5.8 (s, br, 1H), 1.46-1.4(m,2H), 1.31 (s, 12H), 1.0-0.96 (m, 2H).

Step 5: Preparation of N$^2$-[(1S)-1-(4-bromophenyl)-2,2-difluoroethyl]-N$^1$-(1-cyanocyclopropyl)-4-fluoro-L-leucinamide.

Starting from difluoroacetaldehyde ethyl hemiacetal and following the procedure of Example 1 Steps 13-14, the title compound was prepared.

$^1$H NMR (500 MHz, acetone d$_6$) δ 8.2 (s, 1H), 7.56 (d, 2H), 7.4 (d, 2H), 6.15-5.9 (m, 1H), 4.08-3.98 (m, 1H), 3.4-3.34 (m, 1H), 2.66-2.55 (m, 1H), 2.0-1.9 (m, 2H), 1.42-1.34 (m, 8H), 1.05-0.92 (m, 2H).

Step 6: Preparation of N$^2$-((1S)-1-{4'-[1-(aminocarbonyl)cyclopropyl]biphenyl-4-yl}-2,2-difluoroethyl)-N$^1$-(1-cyanocyclopropyl)-4-fluoro-L-leucinamide.

N$^2$-[(1S)-1-(4-bromophenyl)-2,2-difluoroethyl]-N$^1$-(1-cyanocyclopropyl)-4-fluoro-L-leucinamide (11.2 g, 25.9 mmol), 1-[4-(4,4,5,5-tetramethyl-1,3,2-dioxaborolan-2-yl)phenyl]cyclopropanecarboxamide (8.2 g, 28.5 mmol, 1:1 equiv) and 2M sodium carbonate solution (35.4 mL, 70.8 mmol, 2.7 equiv) were mixed in 225 mL N,N-dimethylformamide. The mixture was degassed 3 times with nitrogen, then [1,1'-bis(diphenylphosphino)ferrocene]palladium (II) chloride, 1:1 complex with dichloromethane (838 mg, 1.15 mmol, 0.044 equiv) was added and mixture degassed again 3 times with nitrogen, heated at 80° C. for 6 hours. The reaction mixture was poured into H$_2$O (900 mL), extracted with ethyl acetate (2×250 mL) and dichloromethane (250 mL). Combined organic fractions were washed with brine, dried over sodium sulphate and evaporated. The residue was purified by flash chromatography, eluting first with 1:1 ethyl acetate/hexane, then with 9:1 ethyl acetate/dichloromethane. The light pink recovered solid was stirred in 150 mL of 1:1 ethyl acetate/dichloromethane for 2 hours and filtered to yield the title compound.

$^1$H NMR (500 MHz, acetone d$_6$) δ 8.22 (s, 1H), 7.73-7.67 (m, 4H), 7.58-7.53 (m, 4H), 6.35 (s, 1H), 6.2-5.95 (m, 1H), 5.84 (s, 1H), 4.12-4.04 (m, 1H), 3.49-3.43 (m, 1H), 2.66-2.62 (m, 1H), 2.04-1.93 (m, 2H), 1.5-1.36 (m, 10H), 1.07-1.0 (m, 4H).

MS+ESI 513.2 [M+1]

EXAMPLE 4

Synthesis of N$^1$-(1-cyanocyclopropyl)-N$^2$-[(1S)-1-(4'-{[(1R,2R)-2-[(cyclopropylamino)carbonyl]cyclopropyl}biphenyl-4-yl)-2,2-difluoroethyl]-4-fluoro-L-leucinamide

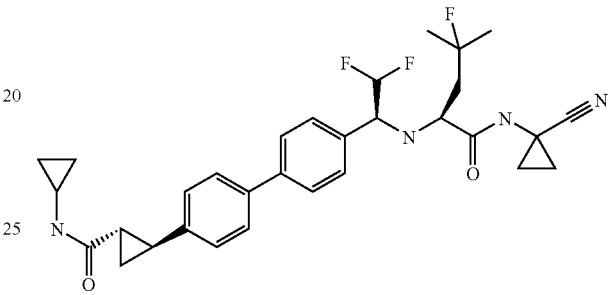

Step 1: (1R,2R)-2-(4-bromophenyl)cyclopropanecarboxylic acid

An enantioselective cyclopropanation analogous to a literature procedure (Evans et al. J. Am. Chem. Soc. 1991, 113, 726) using commercial 2,2'-isopropylidenebis[(4S)-4-tert-butyl-2-oxazoline] in conjunction with copper(I) triflate and ethyldiazoacetate was used to prepare optically active ethyl (1R,2R)-2-(4-bromophenyl)cyclopropanecarboxylate from 4-bromostyrene. The absolute configuration was assigned by analogy based on the sense of the optical rotation. Selective hydrolysis of the trans isomer with LiOH (1 equivalent based on the trans ester) from the mixture of cis and trans esters (that was obtained by the cyclopropanation procedure) gave the title compound.

Step 2: (1R,2R)-2-(4-bromophenyl)-N-cyclopropylcyclopropanecarboxamide

To a solution of (1R,2R)-2-(4-bromophenyl)cyclopropanecarboxylic acid from Step 1 (300 mg, 1.24 mmoles) in dimethylformamide (5 mL) at room temperature was added HATU (500 mg, 1.31 mmoles) followed by cyclopropylamine (0.44 mL, 6.2 mmoles). The reaction mixture was stirred overnight and diluted with half-saturated sodium bicarbonate aqueous solution (50 mL), ether (50 mL) and ethyl acetate (50 mL). The phases were separated and the organic layer was washed with water twice (30 mL each portion), dried over anhydrous sodium sulfate and concentrated under reduced pressure. The residue was purified onto a short column of silica gel using 50% ethyl acetate diethyl ether to give the title compound.

Step 3: N$^1$-(1-cyanocyclopropyl)-N$^2$-[(1S)-2,2-difluoro-1-[4-(4,4,5,5-tetramethyl-1,3,2-dioxaborolan-2-yl)phenyl]ethyl}-4-fluoro-L-leucinamide N$^2$-[(1S)-1-(4-bromophenyl)-2,2-difluoroethyl]-N$^1$-(1-cyanocyclopropyl)-4-fluoro-L-leucinamide was reacted with bis(pinacolato)diboron as described in Example 1, Step 6 to give the title compound.

Step 4: N¹-(1-cyanocyclopropyl)-N²-[(1S)-1-(4'-{[(1R,2R)-2-[(cyclopropylamino) carbonyl]cyclopropyl}biphenyl-4-yl)-2,2-difluoroethyl]-4-fluoro-L-leucinamide To a solution of (1R,2R)-2-(4-bromophenyl)-N-cyclopropylcyclopropanecarboxamide from Step 2 (480 mg, 1.6 mmoles) and N¹-(1-cyanocyclopropyl)-N²-[(1S)-2,2-difluoro-1-[4-(4,4,5,5-tetramethyl-1,3,2-dioxaborolan-2-yl) phenyl]ethyl}-4-fluoro-L-leucinamide from Step 3 (704 mg, 1.46 mmoles) in dimethylformamide (15 mL) at room temperature was added a 2.0 M aqueous solution of sodium carbonate (2.2 mL) and stirred for 5 minutes while bubbling nitrogen via a pipet. The reaction mixture was stirred at 80° C. for 20 h under nitrogen, cooled to room temperature and poured into water (25 mL) and saturated aqueous sodium bicarbonate (75 mL) and ethyl acetate (100 mL). The phases were separated and the aqueous phase extracted twice with 50 mL-portions of ethyl acetate. The combined organic layers were washed with brine (50 mL), dried over anhydrous magnesium sulfate and concentrated under reduced pressure. The residue was purified on silica gel using a gradient from 50% ethyl acetate:toluene to 75% ethyl acetate:25% toluene. The solid was triturated in a mixture of diethyl ether and hexanes followed by a stirring in dichloromethane and hexanes overnight to leave the title compound as a white solid. MS (+ESI): 553.4 [M+1]⁺.

EXAMPLE 5

Synthesis of (2S)-N-((1S)-1-{4'-[1-(aminocarbonyl)cyclopropyl]biphenyl-4-yl}-2,2-difluoroethyl)-1-[(1-cyanocyclopropyl)amino]-4-fluoro-4-methyl-1-oxo-pentan-2-aminium methanesulfonate

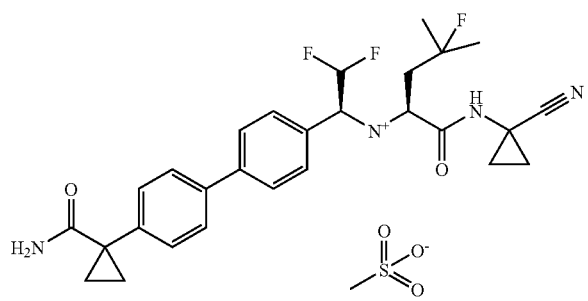

To a solution of N²-((1S)-1-{4'-[1-(aminocarbonyl)cyclopropyl]biphenyl-4-yl}-2,2-difluoroethyl)-N¹-(1-cyanocyclopropyl)-4-fluoro-L-leucinamide (112 mg, 0.219 mmol) in THF (8 mL) was added 0.21 mL of methanesulfonic acid (1M solution in dichloromethane) followed by methyl t-butyl ether (2 mL). Seed crystals were added and the mixture was allowed to stand until a crystal bed had formed. The solvent was removed and the solid was suspended in methyl t-buty ether and heated to reflux overnight. Cooled to room temperature, filtered and dried under vacuum to give the title compound. m.p. 126 C ¹H NMR (400 MHz, methanol d₄) δ 7.82 (d, 2H), 7.70 (d, 2H), 7.62 (d, 2H), 7.55 (d, 2H), 6.41 (dt, 1H), 4.7 (m, 1H), 3.84 (m, 1H), 2.73 (s, 3H), 2.3 (m, 2H), 2.58 (m, 2H), 1.5-1.35 (m, 8H), 1.13 (m, 4H).

EXAMPLE 6

Synthesis of (2S)-1-[(1-cyanocyclopropyl)amino]-N-[(1S)-1-(4'-{(1R,2R)-2-[(cyclopropylamino) carbonyl]cyclopropyl}biphenyl-4-yl)-2,2-difluoroethyl]-4-fluoro-4-methyl-1-oxopentan-2-aminium 4-methylbenzenesulfonate

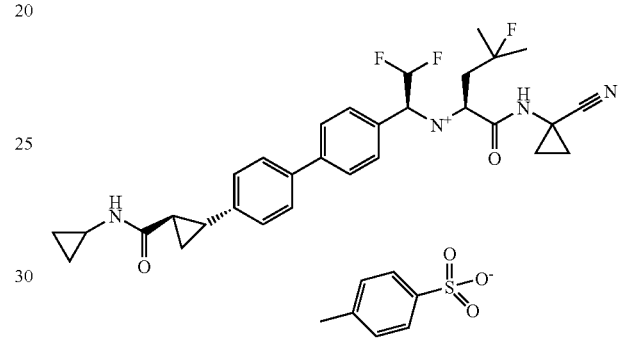

N¹-(1-cyanocyclopropyl)-N²-[(1S)-1-(4'-{(1S,2S)-2-[(cyclopropylamino)carbonyl]cyclopropyl}biphenyl-4-yl)-2,2-difluoroethyl]-4-fluoro-L-leucinamide (60 mg, 0.11 mmol) was dissolved in 0.80 mL of THF. TsOH.H₂O (21 mg, 0.11 mmol) was dissolved in 0.20 mL of THF and was added to the reaction mixture. It was stirred at room temperature for 30 minutes. Hexanes (β3 mL) was then added until a precipitate crashed out of solution. It was sonicated for 5 minutes and it was filtered off on a Buchner funnel. The white solid was dried on the pump overnight. It was triturated in diethyl ether (~5 mL) for 2 h at room temperature and filtered off on a Buchner funnel to yield the title compound.

¹H NMR (CD₃COCD₃) δ 8.80 (br s, 1H), 7.60-7.80 (m, 8H), 7.45 (br s, 1H), 7.22-7.32 (m, 4H), 6.60 (t, 1H), 4.60 (m, 1H), 4.05 (m, 1H), 2.77 (m, 1H), 2.28-2.42 (m, 6H), 1.85 (m, 1H), 1.37-1.53 (m, 9H), 1.23 (m, 1H), 1.12 (m, 2H), 0.65 (m, 2H), 0.47 (m, 2H).

Using similar experimental procedures as those listed above, the following compounds were synthesized.

| Name | Characterization |
|---|---|
| N¹-(1-cyanocyclopropyl)-N²-[(1S)-1-(4'-{1-[(cyclopropylamino)carbonyl]cyclopropyl}biphenyl-4-yl)-2,2-difluoroethyl]-4-fluoro-L-leucinamide | MS (+ESI): 553.0 [M + 1] |
| N²-((1S)-1-{4'-[1-(azetidin-1-ylcarbonyl)cyclopropyl]biphenyl-4-yl}-2,2-difluoroethyl)-N¹-(1-cyanocyclopropyl)-4-fluoro-L-leucinamide | MS (+ESI): 553.1 [M + 1] |
| N¹-(1-cyanocyclopropyl)-N²-{(1S)-2,2-difluoro-1-[4'-(1-{[(2,2,2-trifluoroethyl)amino]carbonyl}cyclopropyl)biphenyl-4-yl]ethyl}-4-fluoro-L-leucinamide | MS (+ESI): 595.0 [M + 1] |

-continued

| Name | Characterization |
|------|------------------|
| N$^1$-(1-cyanocyclopropyl)-N$^2$-((1S)-1-{4'-[2-(cyclopropylamino)-2-oxoethyl]biphenyl-4-yl}-2,2-difluoroethyl)-4-fluoro-L-leucinamide | MS (+ESI): 527.1 [M + 1] |
| N$^1$-(1-cyanocyclopropyl)-N$^2$-[(1S)-2,2-difluoro-1-(4'-{1-[(isopropylamino)carbonyl]cyclopropyl}biphenyl-4-yl)ethyl]-4-fluoro-L-leucinamide | MS (+ESI): 555.3 [M + 1] |
| N$^1$-(1-cyanocyclopropyl)-N$^2$-[(1S)-2,2-difluoro-1-(4'-{1-[(pyridin-3-ylamino)carbonyl]cyclopropyl}biphenyl-4-yl)ethyl]-4-fluoro-L-leucinamide | MS (+ESI): 590.2 [M + 1] |
| N$^1$-(1-cyanocyclopropyl)-N$^2$-{(1S)-2,2-difluoro-1-[4'-(1-{[(2-hydroxyethyl)amino]carbonyl}cyclopropyl)biphenyl-4-yl]ethyl}-4-fluoro-L-leucinamide | MS (+ESI): 557.2 [M + 1] |
| N$^1$-(1-cyanocyclopropyl)-N$^2$-{(1S)-2,2-difluoro-1-[4'-(1-{[(1-methylcyclopropyl)amino]carbonyl}cyclopropyl)biphenyl-4-yl]ethyl}-4-fluoro-L-leucinamide | MS (+ESI): 567.2 [M + 1] |
| N$^1$-(1-cyanocyclopropyl)-N$^2$-{(1S)-2,2-difluoro-1-[4'-(1-{[(2,2,2-trifluoro-1-methylethyl)amino]carbonyl} cyclopropyl)biphenyl-4-yl]ethyl}-4-fluoro-L-leucinamide | MS (+ESI): 609.2 [M + 1] |
| N$^1$-(1-cyanocyclopropyl)-N$^2$-{(1S)-2,2-difluoro-1-[4'-(1-{[(2-fluorocyclopropyl)amino]carbonyl} cyclopropyl)biphenyl-4-yl]ethyl}-4-fluoro-L-leucinamide | MS (+ESI): 571.3 [M + 1] |
| N$^1$-(1-cyanocyclopropyl)-N$^2$-[(1S)-2,2-difluoro-1-(4'-{1-[(1,3-thiazol-2-ylamino)carbonyl]cyclopropyl}biphenyl-4-yl)ethyl]-4-fluoro-L-leucinamide | MS (+ESI): 596.2 [M + 1] |
| N$^2$-{(1S)-1-[4'-(2-amino-1,1-difluoro-2-oxoethyl)biphenyl-4-yl]-2,2,2-trifluoroethyl}-N$^1$-(1-cyanocyclopropyl)4-fluoro-L-leucinamide | MS (+ESI): 541.0 [M + 1] |
| N$^1$-(1-cyanocyclopropyl)-N$^2$-[(1S)-1-(4'-{1-[(cyclopropylamino)carbonyl]cyclopropyl}biphenyl-4-yl)-2,2,2-trifluoroethyl]-4-fluoro-L-leucinamide | MS (+ESI): 571.0 [M + 1] |
| N$^1$-(cyanomethyl)-N$^2$-[(1S)-1-(4'-{1-[(cyclopropylamino)carbonyl]cyclopropyl}biphenyl-4-yl)-2,2,2-trifluoroethyl]-4-fluoro-L-leucinamide | MS (+ESI): 545.2 [M + 1] |
| N$^2$-((1S)-1-{4'-[1-(aminocarbonyl)cyclopropyl]-2'-fluorobiphenyl-4-yl}-2,2,2-trifluoroethyl)-N$^1$-(1-cyanocyclopropyl)-4-fluoro-L-leucinamide | MS (+ESI): 549.0 [M + 1] |
| N$^1$-(1-cyanocyclopropyl)-N$^2$-[(1S)-1-(4'-{1-[(cyclopropylamino)carbonyl]cyclopropyl}biphenyl-4-yl)-2,2-difluoroethyl]-L-leucinamide | MS (+ESI): 535 [M + 1] |
| N$^1$-(1-cyanocyclopropyl)-N$^2$-{(1S)-2,2-difluoro-1-[4'-(1-{[(2,2,2-trifluoroethyl)amino]carbonyl} cyclopropyl)biphenyl-4-yl]ethyl}-L-leucinamide | MS (+ESI): 577 [M + 1] |
| N$^2$-((1S)-1-{4'-[1-(aminocarbonyl)cyclopropyl]biphenyl-4-yl}-2,2-difluoroethyl)-N$^1$-(1-cyanocyclopropyl)-L-leucinamide | MS (+ESI): 495.4 [M + 1] |
| N$^1$-(1-cyanocyclopropyl)-N$^2$-[(1S)-1-(4'-{1-[(cyclopropylamino)carbonyl]cyclobutyl}biphenyl-4-yl)-2,2,2-trifluoroethyl]-4-fluoro-L-leucinamide | MS (+ESI): 585 (MH$^+$) |
| N$^2$-((1S)-1-{4'-[1-(aminocarbonyl)cyclobutyl]biphenyl-4-yl}-2,2,2-trifluoroethyl)-N$^1$-(cyanomethyl)-4-fluoro-L-leucinamide | MS (+ESI): 519 (MH$^+$) |
| N$^2$-((1S)-1-{4'-[1-(aminocarbonyl)cyclobutyl]biphenyl-4-yl}-2,2-difluoroethyl)-N$^1$-(1-cyanocyclopropyl)-4-fluoro-L-leucinamide | MS (+ESI): 527 (MH$^+$) |
| N$^1$-(1-cyanocyclopropyl)-N$^2$-{(1S)-1-[4'-(1-{[(1-cyanocyclopropyl)amino]carbonyl}cyclopropyl)biphenyl-4-yl]-2,2-difluoroethyl}-L-leucinamide | MS (+ESI): 560 [M + 1] |
| N$^1$-(1-cyanocyclopropyl)-N$^2$-{(1S)-2,2-difluoro-1-(4'-{1-[(methoxyamino)carbonyl]cyclopropyl}biphenyl-4-yl)ethyl]-L-leucinamide | MS (+ESI): 525 [M + 1] |
| N$^1$-(1-cyanocyclopropyl)-N$^2$-{(1S)-2,2-difluoro-1-[4'-(1-{[methoxy(methyl)amino]carbonyl}cyclopropyl)biphenyl-4-yl]ethyl}-L-leucinamide | MS (+ESI): 539.2 [M + 1] |
| N$^1$-(1-cyanocyclopropyl)-N$^2$-{(1S)-2,2-difluoro-1-[4'-(1-{[(2-hydroxyethyl)amino]carbonyl}cyclopropyl)biphenyl-4-yl]ethyl}-L-leucinamide | MS (+ESI): 539 [M + 1] |
| N$^1$-(1-cyanocyclopropyl)-N$^2$-[(1S)-1-(4'-{1-[(dimethylamino)carbonyl]cyclopropyl}biphenyl-4-yl)-2,2-difluoroethyl]-4-fluoro-L-leucinamide | MS +APCI 541.0 [M + 1] |
| N$^1$-(1-cyanocyclopropyl)-N$^2$-[(1S)-1-(4'-{1-[(cyclobutylamino)carbonyl]cyclopropyl}biphenyl-4-yl)-2,2-difluoroethyl]-4-fluoro-L-leucinamide | MS +ESI 567.0 [M + 1] |
| N$^1$-(1-cyanocyclopropyl)-N$^2$-((1S)-2,2-difluoro-1-{4'-[1-(pyrrolidin-1-ylcarbonyl)cyclopropyl]biphenyl-4-yl}ethyl)-4-fluoro-L-leucinamide | MS +ESI 567.3 [M + 1] |
| N$^1$-(1-cyanocyclopropyl)-N$^2$-{(1S)-2,2-difluoro-1-[4'-(1-{[methoxy(methyl)amino]carbonyl}cyclopropyl)biphenyl-4-yl]ethyl}-4-fluoro-L-leucinamide | MS +ESI 557.2 [M + 1] |

-continued

| Name | Characterization |
|---|---|
| N¹-(1-cyanocyclopropyl)-N²-{(1S)-2,2-difluoro-1-[4'-(1-{[(2-methoxyethyl)amino]carbonyl}cyclopropyl)biphenyl-4-yl]ethyl}-4-fluoro-L-leucinamide | MS +ESI 571.3 [M + 1] |
| N¹-(1-cyanocyclopropyl)-N²-((1S)-2,2-difluoro-{4'-[1-(morpholin-4-ylcarbonyl)cyclopropyl]biphenyl-4-yl}ethyl)-4-fluoro-L-leucinamide | MS (+ESI) 583.1 [M + 1] |
| N¹-(1-cyanocyclopropyl)-N²-[(1S)-2,2-difluoro-1-(4'-{1-[(methylamino)carbonyl]cyclopropyl}biphenyl-4-yl)ethyl]-4-fluoro-L-leucinamide | MS (+ESI) 527.0 [M + 1] |
| N¹-(1-cyanocyclopropyl)-N²-{(1S)-1-[4'-(1-{[(cyclopropylmethyl)amino]carbonyl}cyclopropyl)biphenyl-4-yl]-2,2-difluoroethyl}-4-fluoro-L-leucinamide | MS (+ESI) 567.3 [M + 1] |
| N¹-(1-cyanocyclopropyl)-N²-[(1S)-2,2-difluoro-1-(4'-{1-[(propylamino)carbonyl]cyclopropyl}biphenyl-4-yl)ethyl]-4-fluoro-L-leucinamide | MS (+ESI) 555.4 [M + 1] |
| N²-((1S)-1-{4'-[1-(aminocarbonyl)cyclopropyl]biphenyl-4-yl}-2,2,2-trifluoroethyl)-N¹-(1-cyanocyclopropyl)-4-fluoro-L-leucinamide | MS (+APCI): 531.3 [M + 1] |
| N¹-(1-cyanocyclopropyl)-N²-{(1S)-1-[4'-(1-{[(cyanomethyl)amino]carbonyl}cyclopropyl)biphenyl-4-yl]-2,2,2-trifluoroethyl}-4-fluoro-L-leucinamide | MS (+APCI): 570.2 [M + 1] |
| N¹-(1-cyanocyclopropyl)-4-fluoro-N²-{(1S)-2,2,2-trifluoro-1-[4'-(1-{[(methylsulfonyl)amino]carbonyl}cyclopropyl)biphenyl-4-yl]ethyl}-L-leucinamide | MS (+APCI): 609.3 [M + 1] |
| N²-[(1S)-1-(4'-{1-[(tert-butylamino)carbonyl]cyclopropyl}biphenyl-4-yl)-2,2,2-trifluoroethyl]-N¹-(1-cyanocyclopropyl)-4-fluoro-L-leucinamide | MS (+APCI): 587.2 [M + 1] |
| N¹-(1-cyanocyclopropyl)-N²-((1S)-1-{4'-[2-(cyclopropylamino)-1,1-dimethyl-2-oxoethyl]biphenyl-4-yl}-2,2,2-trifluoroethyl)-4-fluoro-L-leucinamide | MS (+APCI): 573.1 [M + 1] |
| N¹-(1-cyanocyclopropyl)-N²-[(1S)-1-(4'-{1-[(cyclopropylamino)carbonyl]cyclopropyl}-3'-fluorobiphenyl-4-yl)-2,2,2-trifluoroethyl]-4-fluoro-L-leucinamide | MS (+APCI): 589.1 [M + 1] |
| N¹-(1-cyanocyclopropyl)-N²-[(1S)-1-(4'-{1-[(cyclopropylamino)carbonyl]cyclopropyl}biphenyl-4-yl)-2,2,2-trifluoroethyl]-L-leucinamide | MS (+APCI): 553.4 [M + 1] |
| N¹-(1-cyanocyclopropyl)-N²-[(1S)-1-(4'-{1-[(cyclopropylamino)carbonyl]cyclopropyl}-3'-fluorobiphenyl-4-yl)-2,2,2-difluoroethyl]-4-fluoro-L-leucinamide | MS (+APCI): 571.5 [M + 1] |
| N¹-(1-cyanocyclopropyl)-N²-((1S)-1-{4'-[2-(cyclopropylamino)-1,1-dimethyl-2-oxoethyl]biphenyl-4-yl}-2,2-difluoroethyl)-4-fluoro-L-leucinamide | MS (+APCI): 555.5 [M + 1] |
| N¹-(1-cyanocyclopropyl)-N²-[(1S)-1-(4'-{1-[(cyclopropylamino)carbonyl]cyclopropyl}-2'-fluorobiphenyl-4-yl)-2,2-difluoroethyl]-4-fluoro-L-leucinamide | MS (+APCI): 571.5 [M + 1] |
| N¹-(1-cyanocyclopropyl)-4-fluoro-N²-{(1S)-2,2,2-trifluoro-1-[4'-(1-{[(2-fluorocyclopropyl)amino]carbonyl}cyclopropyl)biphenyl-4-yl]ethyl}-L-leucinamide | MS (+APCI): 589.3 [M + 1] |
| N²-[(1S)-1-(4-{5-[1-(aminocarbonyl)cyclopropyl]-3-chloropyridin-2-yl}phenyl)-2,2,2-trifluoroethyl]-N¹-(1-cyanocyclopropyl)-4-fluoro-L-leucinamide | MS (+APCI): 566.3 [M + 1] |
| N²-{(1S)-1-[4-(3-chloro-5-{1-[(cyclopropylamino)carbonyl]cyclopropyl}pyridin-2-yl)phenyl]-2,2,2-trifluoroethyl}-N¹-(1-cyanocyclopropyl)-4-fluoro-L-leucinamide | MS (+APCI): 606.2 [M + 1] |
| N¹-(1-cyanocyclopropyl)-N²-{(1S)-1-[4-(5-{1-[(cyclopropylamino)carbonyl]cyclopropyl}pyridin-2-yl)phenyl]-2,2,2-trifluoroethyl}-4-fluoro-L-leucinamide | MS (+APCI): 572.4 [M + 1] |
| N²-((1S)-1-{4'-[1-(aminocarbonyl)cyclopropyl]biphenyl-4-yl}-2,2,2-trifluoroethyl)-N¹-(cyanomethyl)-4-fluoro-L-leucinamide | MS (+APCI): 505.1 [M + 1] |
| N²-[(1S)-1-(4-{5-[1-(aminocarbonyl)cyclopropyl]pyridin-2-yl}phenyl)-2,2,2-trifluoroethyl]-N¹-(cyanomethyl)-4-fluoro-L-leucinamide | MS (+APCI): 506.3 [M + 1] |
| N²-{(1S)-1-[4'-(2-amino-1-methyl-2-oxoethyl)biphenyl-4-yl]-2,2,2-trifluoroethyl}-N¹-(1-cyanocyclopropyl)-4-fluoro-L-leucinamide | MS (+ESI): 519.2 [M + 1] |
| N²-((1S)-1-{4'-[(1R)-2-amino-1-methyl-2-oxoethyl]biphenyl-4-yl}-2,2,2-trifluoroethyl)-N¹-(1-cyanocyclopropyl)-4-fluoro-L-leucinamide | MS (+APCI): 519.1 [M + 1] |
| N²-((1S)-1-{4'-[(1S)-2-amino-1-methyl-2-oxoethyl]biphenyl-4-yl}-2,2,2-trifluoroethyl)-N¹-(1-cyanocyclopropyl)-4-fluoro-L-leucinamide | MS (+APCI): 519.2 [M + 1] |
| N²-{(1S)-1-[4'-(2-amino-1-methyl-2-oxoethyl)-2'-fluorobiphenyl-4-yl]-2,2,2-trifluoroethyl}-N¹-(1-cyanocyclopropyl)-4-fluoro-L-leucinamide | MS (+APCI): 536.9 [M + 1] |

-continued

| Name | Characterization |
|---|---|
| $N^2$-((1S)-1-{4-[5-(2-amino-1-methyl-2-oxoethyl)pyridin-2-yl]phenyl}-2,2,2-trifluoroethyl)-$N^1$-(1-cyanocyclopropyl)-4-fluoro-L-leucinamide | MS (+ESI): 520.2 [M + 1] |
| $N^2$-{(1S)-1-[4'-(2-amino-1-methyl-2-oxoethyl)-2'-fluorobiphenyl-4-yl]-2,2-difluoroethyl}-$N^1$-(1-cyanocyclopropyl)-4-fluoro-L-leucinamide | MS (+ESI): 519.1 [M + 1] |
| $N^2$-((1S)-1-{4'-[(1R)-2-amino-1-methyl-2-oxoethyl]-2'-fluorobiphenyl-4-yl}-2,2,2-trifluoroethyl)-$N^1$-(1-cyanocyclopropyl)-4-fluoro-L-leucinamide | MS (+APCI): 537.1 [M + 1] |
| $N^2$-((1S)-1-{4'-[(1S)-2-amino-1-methyl-2-oxoethyl]-2'-fluorobiphenyl-4-yl}-2,2,2-trifluoroethyl)-$N^1$-(1-cyanocyclopropyl)-4-fluoro-L-leucinamide | MS (+APCI): 537.1 [M + 1] |
| $N^2$-((1S)-1-{4'-[(1S)-2-amino-1-methyl-2-oxoethyl]-2-bromobiphenyl-4-yl}-2,2,2-trifluoroethyl)-$N^1$-(1-cyanocyclopropyl)-4-fluoro-L-leucinamide | MS (+APCI): 597.0, 599.1 [M + 1] |
| $N^2$-((1S)-1-{4'-[(1S)-2-amino-1-methyl-2-oxoethyl]biphenyl-4-yl}-2,2,2-trifluoroethyl)-$N^1$-(1-cyanocyclopropyl)-4-fluoro-5-hydroxy-L-leucinamide | MS (+ESI): 535.1 [M + 1] |
| 1-(4'-{(1S)-1-[((1S)-1-{[(1-cyanocyclopropyl)amino]carbonyl}-3,3,3-trifluoropropyl)amino]-2,2,2-trifluoroethyl}biphenyl-4-yl)cyclopropanecarboxamide | MS (+APCI): 539.4 [M + 1] |
| $N^2$-((1S)-1-{4'-[1-(aminocarbonyl)vinyl]biphenyl-4-yl}-2,2,2-trifluoroethyl)-$N^1$-(1-cyanocyclopropyl)-4-fluoro-L-leucinamide | MS (+ESI): 517.1 [M + 1] |
| $N^2$-((1S)-1-{4'-[1-(aminocarbonyl)cyclopropyl]biphenyl-4-yl}-2,2,2-trifluoroethyl)-$N^1$-(1-cyanocyclopropyl)-L-norvalinamide | MS (+ESI): 499.0 [M + 1] |
| $N^2$-((1S)-1-{4'-[1-(2-amino-2-oxoethyl)cyclopropyl]biphenyl-4-yl}-2,2,2-trifluoroethyl)-$N^1$-(1-cyanocyclopropyl)-4-fluoro-L-leucinamide | MS (+ESI): 545.2 [M + 1] |
| $N^2$-{(1S)-1-[4'-(3-amino-2,2-dimethyl-3-oxopropyl)biphenyl-4-yl]-2,2,2-trifluoroethyl}-$N^1$-(1-cyanocyclopropyl)-4-fluoro-L-leucinamide | MS (+ESI): 547.2 [M + 1] |
| $N^2$-{(1S)-1-[4'-(2-amino-2-oxoethyl)-2'-fluorobiphenyl-4-yl]-2,2,2-trifluoroethyl}-$N^1$-(1-cyanocyclopropyl)-4-fluoro-L-leucinamide | MS (+ESI): 523.0 [M + 1] |
| $N^2$-{(1S)-1-[4'-(2-amino-2-oxoethyl)biphenyl-4-yl]-2,2,2-trifluoroethyl}-$N^1$-(1-cyanocyclopropyl)-4-fluoro-L-leucinamide | MS (+ESI): 505.1 [M + 1] |

Pharmaceutical Composition

As a specific embodiment of this invention, 100 mg of $N^1$-(1-cyanocyclopropyl)-$N^2$-{(1S)-1-[4-(6-{1-[(cyclopropylamino)carbonyl]cyclopropyl}-2-fluoropyridin-3-yl)phenyl]-2,2,2-trifluoroethyl}-4-fluoro-L-leucinamide is formulated with sufficient finely divided lactose to provide a total amount of 580 to 590 mg to fill a size 0, hard-gelatin capsule.

The compounds disclosed in the present application exhibited activity in the following assays. In addition, the compounds disclosed in the present application have an enhanced pharmacological profile relative to previously disclosed compounds.

Cathepsin K Assay

Serial dilutions (1/3) from 500 μM down to 0.0085 μM of test compounds were prepared in dimethyl sulfoxide (DMSO). Then 2 μL of DMSO from each dilution were added to 50 μL of assay buffer (MES, 50 mM (pH 5.5); EDTA, 2.5 mM; DTT, 2.5 mM and 10% DMSO) and 25 μL of human cathepsin K (0.4 nM) in assay buffer solution. The assay solutions were mixed for 5-10 seconds on a shaker plate and incubated for 15 minutes at room temperature. Z-Leu-Arg-AMC (8 μM) in 25 μL of assay buffer was added to the assay solutions. Hydrolysis of the coumarin leaving group (AMC) was followed by spectrofluorometry (Exλ=355 nm; Emλ=460 nm) for 10 minutes. Percent of inhibition were calculated by fitting experimental values to standard mathematical model for dose response curve.

Cathepsin L Assay

Serial dilutions (1/3) from 500 μM down to 0.0085 μM of test compounds were prepared in dimethyl sulfoxide (DMSO). Then 2 μL of DMSO from each dilution were added to 50 μL of assay buffer (MES, 50 mM (pH 5.5); EDTA, 2.5 mM; DTT, 2.5 mM and 10% DMSO) and 25 μL of human cathepsin L (0.5 nM) in assay buffer solution. The assay solutions were mixed for 5-10 seconds on a shaker plate and incubated for 15 minutes at room temperature. Z-Leu-Arg-AMC (8 μM) in 25 μL of assay buffer was added to the assay solutions. Hydrolysis of the coumarin leaving group (AMC) was followed by spectrofluorometry (Exλ=355 nm; Emλ=460 nm) for 10 minutes. Percent of inhibition were calculated by fitting experimental values to standard mathematical model for dose response curve.

Cathepsin B Assay

Serial dilutions (1/3) from 500 μM down to 0.0085 μM of test compounds were prepared in dimethyl sulfoxide (DMSO). Then 2 μL of DMSO from each dilution were added to 50 μL of assay buffer (MES, 50 mM (pH 5.5); EDTA, 2.5 mM; DTT, 2.5 mM and 10% DMSO) and 25 μL of human cathepsin B (4.0 nM) in assay buffer solution. The assay solutions were mixed for 5-10 seconds on a shaker plate and incubated for 15 minutes at room temperature. Z-Leu-Arg-AMC (8 μM) in 25 μL of assay buffer was added to the assay solutions. Hydrolysis of the coumarin leaving group (AMC) was followed by spectrofluorometry (Exλ=355 nm; Emλ=460 nm) for 10 minutes. Percent of inhibition were calculated by fitting experimental values to standard mathematical model for dose response curve.

Cathepsin S Assay

Serial dilutions (1/3) from 500 μM down to 0.0085 μM of test compounds were prepared in dimethyl sulfoxide (DMSO). Then 2 µL of DMSO from each dilution were added to 50 µL of assay buffer (MES, 50 mM (pH 5.5); EDTA, 2.5 mM; DTT, 2.5 mM and 10% DMSO) and 25 µL of human cathepsin S (20 nM) in assay buffer solution. The assay solutions were mixed for 5-10 seconds on a shaker plate and incubated for 15 minutes at room temperature. Z-Leu-Arg-AMC (8 µM) in 25 µL of assay buffer was added to the assay solutions. Hydrolysis of the coumarin leaving group (AMC) was followed by spectrofluorometry (Exλ=355 nm; Emλ=460 nm) for 10 minutes. Percent of inhibition were calculated by fitting experimental values to standard mathematical model for dose response curve.

The invention claimed is:

1. A compound of the formula:

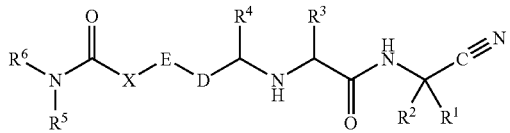

wherein $R^1$ is hydrogen, $C_{1-6}$ alkyl or $C_{2-6}$ alkenyl wherein said alkyl and alkenyl groups are optionally substituted with one to six halo, $C_{3-6}$ cycloalkyl, —$SR^7$, —$SOR^7$, —$SO_2R^7$, —$SO_2CH(R^a)(R^b)$, —$OR^7$, —$N(R^7)_2$, aryl, heteroaryl or heterocyclyl wherein said aryl, heteroaryl and heterocyclyl groups are optionally substituted with one or two substitutents independently selected from $C_{1-6}$ alkyl, halo, hydroxyalkyl, hydroxy, alkoxy or keto;

$R^2$ is hydrogen, $C_{1-6}$ alkyl or $C_{2-6}$ alkenyl wherein said alkyl and alkenyl groups are optionally substituted with one to six halo, $C_{3-6}$ cycloalkyl, —$SR^7$, —$SOR^7$, —$SO_2R^7$,—$SO_2CH(R^a)(R^b)$, —$OR^7$, —$N(R^7)_2$, aryl, heteroaryl or heterocyclyl wherein said aryl, heteroaryl and heterocyclyl groups are optionally substituted with one or two substitutents independently selected from $C_{1-6}$ alkyl, halo, hydroxyalkyl, hydroxy, alkoxy or keto;

or $R^1$ and $R^2$ can be taken together with the carbon atom to which they are attached to form a $C_{3-8}$ cycloalkyl or heterocyclyl ring wherein said ring system is optionally substituted with one or two substituents independently selected from $C_{1-6}$ alkyl, hydroxyalkyl, haloalkyl or halo;

$R^3$ is $C_{1-6}$ alkyl or $C_{2-6}$ alkenyl, wherein said alkyl and alkenyl groups are optionally substituted with $C_{3-6}$ cycloalkyl or one to six halo;

$R^4$ is $C_{1-6}$ alkyl substituted with 1-6 halo;

$R^5$ is selected from hydrogen or $C_{1-3}$ alkyl;

D is aryl or heteroaryl, wherein said aryl or heteroaryl group, which may be monocyclic or bicyclic, is optionally substituted on either the carbon or the heteroatom with one to five substituents independently selected from $C_{1-6}$ alkyl, haloalkyl, halo, keto, alkoxy, —$SR^7$, —$OR^7$, $N(R^7)_2$, —$SO_2R^7$ or —$SO_2R^a$;

E is aryl or heteroaryl, wherein said aryl or heteroaryl group, which may be monocyclic or bicyclic, is optionally substituted on either the carbon or the heteroatom with one to five substituents independently selected from $C_{1-6}$ alkyl, haloalkyl, halo, keto, alkoxy, —$SR^7$, —$OR^7$, $N(R^7)_2$ or —$SO_2R^7$;

X is $CR^aR^b$ or cyclopropyl;

$R^7$ is selected from hydrogen, $C_{1-6}$ alkyl, aryl, aryl($C_{1-4}$) alkyl, heteroaryl, heteroaryl($C_{1-4}$) alkyl, $C_{3-8}$cycloalkyl, $C_{3-8}$cycloalkyl($C_{1-4}$)alkyl, and heterocyclyl ($C_{1-4}$)alkyl wherein said groups can be optionally substituted with one, two, or three substituents independently selected from halo, alkoxy, cyano, —$NR^aR^b$, —$SR^a$ or —$SO_mR^a$;

$R^6$ is selected hydrogen, $C_{1-6}$ alkyl, $C_{3-8}$ cycloalkyl, heterocyclyl, heteroaryl, cyano, halo, alkoxy, $OR^a$, —$NR^a$, —$SR^a$ or —$SO_mR^5$; wherein said alkyl, cycloalkyl, heterocyclyl and heteroaryl groups can be optionally substituted with one, two, or three substituents independently selected from halo, cyano or —$OR^a$;

$R^a$ is hydrogen or $C_{1-6}$ alkyl which is optionally substituted with one, two, or three substituents independently selected from halo or —$OR^5$;

$R^b$ is hydrogen or $C_{1-6}$ alkyl which is optionally substituted with one, two, or three substituents independently selected from halo or —$OR^5$;

m is an integer from zero to two;

or a pharmaceutically acceptable salt or stereoisomer thereof.

2. The compound of claim 1 wherein $R^1$ is hydrogen, $R^2$ is hydrogen, or $R^1$ and $R^2$ can be taken together with the carbon atom to which they are attached to form a $C_{3-8}$ cycloalkyl ring.

3. The compound of claim 2 wherein $R^3$ is $C_{1-6}$ alkyl optionally substituted with one to six halo.

4. The compound of claim 3 wherein D is aryl.

5. The compound of claim 4 wherein D is phenyl.

6. The compound of claim 1 wherein X is cyclopropyl.

7. The compound selected from:

$N^1$-(1-cyanocyclopropyl)-$N^2$-[(1S)-1-(4'-{1-[(cyclopropylamino)carbonyl]cyclopropyl}-2'-fluorobiphenyl-4-yl)-2,2,2-trifluoroethyl]-4-fluoro-L-leucinamide;

$N^2$-[(1S)-1-(4-{5-[1-(aminocarbonyl)cyclopropyl]pyridin-2-yl}phenyl)-2,2,2-trifluoroethyl]-$N^1$-(1-cyanocyclopropyl)-4-fluoro-L-leucinamide;

$N^2$-((1S)-1-{4'-[1-(aminocarbonyl)cyclopropyl]biphenyl-4-yl}-2,2-difluoroethyl)-$N^1$-(1-cyanocyclopropyl)-4-fluoro-L-leucinamide;

$N^1$-(1-cyanocyclopropyl)-$N^2$-[(1S)-1-(4'-{[(1R,2R)-2-[(cyclopropylamino)carbonyl]cyclopropyl}biphenyl-4-yl)-2,2-difluoroethyl]-4-fluoro-L-leucinamide;

$N^1$-(1-cyanocyclopropyl)-$N^2$-[(1S)-1-(4'-{1-[(cyclopropylamino)carbonyl]cyclopropyl}biphenyl-4-yl)-2,2-difluoroethyl]-4-fluoro-L-leucinamide;

$N^2$-((1S)-1-{4'-[1-(azetidin-1-ylcarbonyl)cyclopropyl]biphenyl-4-yl}-2,2-difluoroethyl)-$N^1$-(1-cyanocyclopropyl)-4-fluoro-L-leucinamide;

$N^1$-(1-cyanocyclopropyl)-$N^2$-{(1S)-2,2-difluoro-1-[4'-(1-{[(2,2,2-trifluoroethyl)amino]carbonyl}cyclopropyl)biphenyl-4-yl]ethyl}-4-fluoro-L -leucinamide;

$N^1$-(1-cyanocyclopropyl)-$N^2$-((1S)-1-{4'-[2-(cyclopropylamino)-2-oxoethyl]biphenyl-4-yl}-2,2-difluoroethyl)-4-fluoro-L-leucinamide;

$N^1$-(1-cyanocyclopropyl)-$N^2$-[(1S)-2,2-difluoro-1-(4'-{1-[(isopropylamino)carbonyl]cyclopropyl}biphenyl-4-yl)ethyl]-4-fluoro-L-leucinamide;

$N^1$-(1-cyanocyclopropyl)-$N^2$-[(1S)-2,2-difluoro-1-(4'-{1[(pyridin-3-ylamino)carbonyl]cyclopropyl}biphenyl-4-yl)ethyl]-4-fluoro-L-leucinamide;

$N^1$-(1-cyanocyclopropyl)-$N^2$-{(1S)-2,2-difluoro-1[4'-(1-{[(2-hydroxyethyl)amino]carbonyl}cyclopropyl)biphenyl-4-yl]ethyl}-4-fluoro-L-leucinamide;

$N^1$-(1-cyanocyclopropyl)-$N^2$-{(1S)-2,2-difluoro-1[4'-(1-{[(1-methylcyclopropyl)amino]carbonyl}cyclopropyl)biphenyl-4-yl]ethyl}-4-fluoro-L-leucinamide;

$N^1$-(1-cyanocyclopropyl)-$N^2$-{(1S)-2,2-difluoro-1-[4'-(1-{[(2,2,2-trifluoro-1-methylethyl)amino]carbonyl}cyclopropyl)biphenyl-4-yl]ethyl}-4-fluoro-L-leucinamide;

$N^1$-(1-cyanocyclopropyl)-$N^2$-{(1S)-2,2-difluoro-1-[4'-(1-{[(2-fluorocyclopropyl)amino]carbonyl}cyclopropyl)biphenyl-4-yl]ethyl}-4-fluoro-L-leucinamide;

$N^1$-(1-cyanocyclopropyl)-$N^2$-[(1S)-2,2-difluoro-1-(4'-{1-[(1,3-thiazol-2-ylamino)carbonyl]cyclopropyl}biphenyl-4-yl)ethyl]-4-fluoro-L-leucinamide;

$N^2$-{(1S)-1-[4'-(2-amino-1,1-difluoro-2-oxoethyl)biphenyl-4-yl]-2,2,2-trifluoroethyl}-$N^1$-(1-cyanocyclopropyl)-4-fluoro-L-leucinamide;

$N^1$-(1-cyanocyclopropyl)-$N^2$-[(1S)-1-(4'-{1-[(cyclopropylamino)carbonyl]cyclopropyl}biphenyl-4-yl)-2,2,2-trifluoroethyl]-4-fluoro-L-leucinamide;

$N^1$-(cyanomethyl)-$N^2$-[(1S)-1-(4'-{1-[(cyclopropylamino)carbonyl]cyclopropyl}biphenyl-4-yl)-2,2,2-trifluoroethyl]-4-fluoro-L-leucinamide;

$N^2$-((1S)-1-{4'-[1-(aminocarbonyl)cyclopropyl]-2'-fluorobiphenyl-4-yl}-2,2,2-trifluoroethyl)-$N^1$-(1-cyanocyclopropyl)-4-fluoro-L-leucinamide;

$N^1$-(1-cyanocyclopropyl)-$N^2$-[(1S)-1-(4'-{1-[(cyclopropylamino)carbonyl]cyclopropyl}biphenyl-4-yl)-2,2-difluoroethyl]-L-leucinamide;

$N^1$-(1-cyanocyclopropyl)-$N^2$-{(1S)-2,2-difluoro-1-[4'-(1-{[(2,2,2-trifluoroethyl)amino]carbonyl}cyclopropyl)biphenyl-4-yl]ethyl}-L-leucinamide;

$N^2$-((1S)-1-{4'-[1-(aminocarbonyl)cyclopropyl]biphenyl-4-yl}-2,2-difluoroethyl)-$N^1$-(1-cyanocyclopropyl)-L-leucinamide;

$N^1$-(1-cyanocyclopropyl)-$N^2$-[(1S)-1-(4'-{1-[(cyclopropylamino)carbonyl]cyclobutyl}biphenyl-4-yl)-2,2,2-trifluoroethyl]-4-fluoro-L-leucinamide;

$N^2$-((1S)-1-{4'-[1-(aminocarbonyl)cyclobutyl]biphenyl-4-yl}-2,2,2-trifluoroethyl)-$N^1$-(cyanomethyl)-4-fluoro-L-leucinamide;

$N^2$-((1S)-1-{4'-[1-(aminocarbonyl)cyclobutyl]biphenyl-4-yl}-2,2-difluoroethyl)-$N^1$-(1-cyanocyclopropyl)-4-fluoro-L-leucinamide;

$N^1$-(1-cyanocyclopropyl)-$N^2$-{(1S)-1-[4'-(1-{[(1-cyanocyclopropyl)amino]carbonyl}cyclopropyl)biphenyl-4-yl]-2,2-difluoroethyl}-L-leucinamide;

$N^1$-(1-cyanocyclopropyl)-$N^2$-{(1S)-2,2-difluoro-1-(4'-{1-[(methoxyamino)carbonyl]cyclopropyl}biphenyl-4-yl)ethyl]-L-leucinamide;

$N^1$-(1-cyanocyclopropyl)-$N^2$-{(1S)-2,2-difluoro-1-[4'-(1-{[methoxy(methyl)amino]carbonyl}cyclopropyl)biphenyl-4-yl]ethyl}-L-leucinamide;

$N^1$-(1-cyanocyclopropyl)-$N^2$-{(1S)-2,2-difluoro-1-[4'-(1-{[(2-hydroxyethyl)amino]carbonyl}cyclopropyl)biphenyl-4-yl]ethyl}-L-leucinamide;

$N^1$-(1-cyanocyclopropyl)-$N^2$-[(1S)-1-(4'-{1-[(dimethylamino)carbonyl]cyclopropyl}biphenyl-4-yl)-2,2-difluoroethyl]-4-fluoro-L-leucinamide;

$N^1$-(1-cyanocyclopropyl)-$N^2$-[(1S)-1-(4'-{1-[(cyclobutylamino)carbonyl]cyclopropyl}biphenyl-4-yl)-2,2-difluoroethyl]-4-fluoro-L-leucinamide;

$N^1$-(1-cyanocyclopropyl)-$N^2$-((1S)-2,2-difluoro-1-{4'-[1-(pyrrolidin-1-ylcarbonyl)cyclopropyl]biphenyl-4-yl}ethyl)-4-fluoro-L-leucinamide;

$N^1$-(1-cyanocyclopropyl)-$N^2$-{(1S)-2,2-difluoro-1-[4'-(1-{[methoxy(methyl)amino]carbonyl}cyclopropyl)biphenyl-4-yl]ethyl}-4-fluoro-L-leucinamide;

$N^1$-(1-cyanocyclopropyl)-$N^2$-{(1S)-2,2-difluoro-1-[4'-(1-{[(2-methoxyethyl)amino]carbonyl}cyclopropyl)biphenyl-4-yl]ethyl}-4-fluoro-L-leucinamide;

$N^1$-(1-cyanocyclopropyl)-$N^2$-((1S)-2,2-difluoro-1-{4'-[1-(morpholin-4-ylcarbonyl)cyclopropyl]biphenyl-4-yl}ethyl)-4-fluoro-L-leucinamide;

$N^1$-(1-cyanocyclopropyl)-$N^2$-[(1S)-2,2-difluoro-1-(4'-{1-[(methylamino)carbonyl]cyclopropyl}biphenyl-4-yl)ethyl]-4-fluoro-L-leucinamide;

$N^1$-(1-cyanocyclopropyl)-$N^2$-{(1S)-1-[4'-(1-{[(cyclopropylmethyl)amino]carbonyl}cyclopropyl)biphenyl-4-yl]-2,2-difluoroethyl}-4-fluoro-L-leucinamide;

$N^1$-(1-cyanocyclopropyl)-$N^2$-[(1S)-2,2-difluoro-1-(4'-{1-[(propylamino)carbonyl]cyclopropyl}biphenyl-4-yl)ethyl]-4-fluoro-L-leucinamide;

$N^2$-((1S)-1-{4'-[1-(aminocarbonyl)cyclopropyl]biphenyl-4-yl}-2,2,2-trifluoroethyl)-$N^1$-(1-cyanocyclopropyl)-4-fluoro-L-leucinamide;

$N^1$-(1-cyanocyclopropyl)-$N^2$-{(1S)-1-[4'-(1-{[(cyanomethyl)amino]carbonyl}cyclopropyl)biphenyl-4-yl]-2,2,2-trifluoroethyl}-4-fluoro-L-leucinamide;

$N^1$-(1-cyanocyclopropyl)-4-fluoro-$N^2$-{(1S)-2,2,2-trifluoro-1-[4'-(1-{[(methylsulfonyl)amino]carbonyl}cyclopropyl)biphenyl-4-yl]ethyl}-L-leucinamide;

$N^2$-[(1S)-1-(4'-{1-[(tert-butylamino)carbonyl]cyclopropyl}biphenyl-4-yl)-2,2,2-trifluoroethyl]-$N^1$-(1-cyanocyclopropyl)-4-fluoro-L-leucinamide;

$N^1$-(1-cyanocyclopropyl)-$N^2$-((1S)-1-{4'-[2-(cyclopropylamino)-1,1-dimethyl-2-oxoethyl]biphenyl-4-yl}-2,2,2-trifluoroethyl)-4-fluoro-L-leucinamide;

$N^1$-(1-cyanocyclopropyl)-$N^2$-[(1S)-1-(4'-{1-[(cyclopropylamino)carbonyl]cyclopropyl}-3'-fluorobiphenyl-4-yl)-2,2,2-trifluoroethyl]-4-fluoro-L-leucinamide;

$N^1$-(1-cyanocyclopropyl)-$N^2$-[(1S)-1-(4'-{1-[(cyclopropylamino)carbonyl]cyclopropyl}biphenyl-4-yl)-2,2,2-trifluoroethyl]-L-leucinamide;

$N^1$-(1-cyanocyclopropyl)-$N^2$-[(1S)-1-(4'-{1-[(cyclopropylamino)carbonyl]cyclopropyl}-3'-fluorobiphenyl-4-yl)-2,2-difluoroethyl]-4-fluoro-L-leucinamide;

$N^1$-(1-cyanocyclopropyl)-$N^2$-((1S)-1-{4'-[2-(cyclopropylamino)-1,1-dimethyl-2-oxoethyl]biphenyl-4-yl}-2,2-difluoroethyl)-4-fluoro-L-leucinamide;

$N^1$-(1-cyanocyclopropyl)-$N^2$-[(1S)-1-(4'-{1-[(cyclopropylamino)carbonyl]cyclopropyl}-2'-fluorobiphenyl-4-yl)-2,2-difluoroethyl]-4-fluoro-L-leucinamide;

$N^1$-(1-cyanocyclopropyl)-4-fluoro-$N^2$-{(1S)-2,2,2-trifluoro-1-[4'-(1-{[(2-fluorocyclopropyl)amino]carbonyl}cyclopropyl)biphenyl-4-yl]ethyl}-L-leucinamide;

$N^2$-[(1S)-1-(4-{5-[1-(aminocarbonyl)cyclopropyl]-3-chloropyridin-2-yl}phenyl)-2,2,2-trifluoroethyl]-$N^1$-(1-cyanocyclopropyl)-4-fluoro-L-leucinamide;

$N^2$-{(1S)-1-[4-(3-chloro-5-{1-[(cyclopropylamino)carbonyl]cyclopropyl}pyridin-2-yl)phenyl]-2,2,2-trifluoroethyl}-$N^1$-(1-cyanocyclopropyl)-4-fluoro-L-leucinamide;

$N^1$-(1-cyanocyclopropyl)-$N^2$-{(1S)-1-[4-(5-{1-[(cyclopropylamino)carbonyl]cyclopropyl}pyridin-2-yl)phenyl]-2,2,2-trifluoroethyl}-4-fluoro-L-leucinamide;

$N^2$-((1S)-1-{4'-[1-(aminocarbonyl)cyclopropyl]biphenyl-4-yl}-2,2,2-trifluoroethyl)-$N^1$-(cyanomethyl)-4-fluoro-L-leucinamide;

$N^2$-[(1S)-1-(4-{5-[1-(aminocarbonyl)cyclopropyl]pyridin-2-yl}phenyl)-2,2,2-trifluoroethyl]-$N^1$-(cyanomethyl)-4-fluoro-L-leucinamide;

$N^2$-{(1S)-1-[4'-(2-amino-1-methyl-2-oxoethyl)biphenyl-4-yl]-2,2,2-trifluoroethyl}-$N^1$-(1-cyanocyclopropyl)-4-fluoro-L-leucinamide;

$N^2$-((1S)-1-{4'-[(1R)-2-amino-1-methyl-2-oxoethyl]biphenyl-4-yl}-2,2,2-trifluoroethyl)-$N^1$-(1-cyanocyclopropyl)-4-fluoro-L-leucinamide;

N²-((1S)-1-{4'-[(1S)-2-amino-1-methyl-2-oxoethyl]biphenyl-4-yl}-2,2,2-trifluoroethyl)-N¹-(1-cyanocyclopropyl)-4-fluoro-L-leucinamide;

N²-{(1S)-1-[4'-(2-amino-1methyl-2-oxoethyl)-2'-fluorobiphenyl-4-yl]-2,2,2-trifluoroethyl}-N¹-(1-cyanocyclopropyl)-4-fluoro-L-leucinamide;

N²-((1S)-1-{4-[5-(2-amino-1-methyl-2-oxoethyl)pyridin-2-yl]phenyl}-2,2,2-trifluoroethyl)-N¹-(1-cyanocyclopropyl)-4-fluoro-L-leucinamide;

N²-{(1S)-1-[4'-(2-amino-1-methyl-2-oxoethyl)-2'-fluorobiphenyl-4-yl]-2,2-difluoroethyl}-N¹-(1-cyanocyclopropyl)-4-fluoro-L-leucinamide;

N²-((1S)-1-{4'-[(1R)-2-amino-1-methyl-2-oxoethyl]-2'-fluorobiphenyl-4-yl}-2,2,2-trifluoroethyl)-N¹-(1-cyanocyclopropyl)-4-fluoro-L-leucinamide;

N²-((1S)-1-{4'-[(1S)-2-amino-1-methyl-2-oxoethyl]-2'-fluorobiphenyl-4-yl}-2,2,2-trifluoroethyl)-N¹-(1-cyanocyclopropyl)-4-fluoro-L-leucinamide;

N²-((1S)-1-{4'-[(1S)-2-amino-1-methyl-2-oxoethyl]-2-bromobiphenyl-4-yl}-2,2,2-trifluoroethyl)-N¹-(1-cyanocyclopropyl)-4-fluoro-L-leucinamide;

N²-((1S)-1-{4'-[(1S)-2-amino-1-methyl-2-oxoethyl]biphenyl-4-yl}-2,2,2-trifluoroethyl)-N¹-(1-cyanocyclopropyl)-4-fluoro-5-hydroxy-L-leucinamide;

1-(4'-{(1S)-1-[((1S)-1-{[(1-cyanocyclopropyl)amino]carbonyl}-3,3,3-trifluoropropyl)amino]-2,2,2-trifluoroethyl}biphenyl-4-yl)cyclopropanecarboxamide;

N²-((1S)-1-{4'-[1-(aminocarbonyl)vinyl]biphenyl-4-yl}-2,2,2-trifluoroethyl)-N¹-(1-cyanocyclopropyl)-4-fluoro-L-leucinamide;

N²-((1S)-1-{4'-[1-(aminocarbonyl)cyclopropyl]biphenyl-4-yl}-2,2,2-trifluoroethyl)-N¹-(1-cyanocyclopropyl)-L-norvalinamide;

N²-((1S)-1-{4'-[1-(2-amino-2-oxoethyl)cyclopropyl]biphenyl-4-yl}-2,2,2-trifluoroethyl)-N¹-(1-cyanocyclopropyl)-4-fluoro-L-leucinamide;

N²-{(1S)-1-[4'-(3-amino-2,2-dimethyl-3-oxopropyl)biphenyl-4-yl]-2,2,2-trifluoroethyl}-N¹-(1-cyanocyclopropyl)-4-fluoro-L-leucinamide;

N²-{(1S)-1-[4'-(2-amino-2-oxoethyl)-2'-fluorobiphenyl-4-yl]-2,2,2-trifluoroethyl}-N¹-(1-cyanocyclopropyl)-4-fluoro-L-leucinamide;

N²-{(1S)-1-[4'-(2-amino-2-oxoethyl)biphenyl-4-yl]-2,2,2-trifluoroethyl}-N¹-(1-cyanocyclopropyl)-4-fluoro-L-leucinamide;

or a pharmaceutically acceptable salt or stereoisomer thereof.

8. A pharmaceutical composition comprising a compound according to claim 1 and a pharmaceutically acceptable carrier.

9. A pharmaceutical composition comprising a compound of claim 1 and another agent selected from the group consisting of: an organic bisphosphonate, an estrogen receptor modulator, an estrogen receptor beta modulator, an androgen receptor modulator, an inhibitor of osteoclast proton ATPase, an inhibitor of HMG-CoA reductase, an integrin receptor antagonist, or an osteoblast anabolic agent, and the pharmaceutically acceptable salts and mixtures thereof.

* * * * *